(12) United States Patent
Kim

(10) Patent No.: US 9,877,749 B2
(45) Date of Patent: Jan. 30, 2018

(54) SYSTEMS AND METHODS FOR POSTERIOR DYNAMIC STABILIZATION OF THE SPINE

(71) Applicant: The Board of Trustees of the Leland Stanford Junior University, Palo Alto, CA (US)

(72) Inventor: Daniel H. Kim, Houston, TX (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 14/528,963

(22) Filed: Oct. 30, 2014

(65) Prior Publication Data

US 2015/0150604 A1 Jun. 4, 2015

Related U.S. Application Data

(63) Continuation of application No. 13/461,026, filed on May 1, 2012, now Pat. No. 8,900,271, which is a
(Continued)

(51) Int. Cl.
*A61B 17/70* (2006.01)
*A61B 17/00* (2006.01)

(52) U.S. Cl.
CPC .......... *A61B 17/7065* (2013.01); *A61B 17/70* (2013.01); *A61B 17/7068* (2013.01); *A61B 2017/00557* (2013.01)

(58) Field of Classification Search
CPC .................... A61F 2/441; A61F 2/4611; A61F 2/7062–2/7068; A61B 17/7065;
(Continued)

(56) References Cited

U.S. PATENT DOCUMENTS 2,248,054 A 7/1941 Becker
2,677,369 A 5/1954 Knowles
(Continued)

FOREIGN PATENT DOCUMENTS

CA 268461 A 2/1927
CN 2794456 Y 7/2006
(Continued)

OTHER PUBLICATIONS

European Search Report Application No. EP05849654.8; Applicant: The Board of Trustees of the Leland Stanford Junior University; dated Jun. 21, 2011, 4 pages.
(Continued)

*Primary Examiner* — Christopher D Prone
(74) *Attorney, Agent, or Firm* — Perkins Coie LLP

(57) ABSTRACT

Devices, systems and methods for dynamically stabilizing the spine are provided. The devices include an expandable spacer or member having an unexpanded configuration and an expanded configuration, wherein the expandable member in an expanded configuration has a size, volume and/or shape configured for positioning between the spinous processes of adjacent vertebrae in order to distract the vertebrae relative to each other. The systems include one or more expandable members and an expansion medium for injection within or for filling the interior of the expandable member via the port. The methods involve the implantation of one or more devices or expandable spacers.

33 Claims, 14 Drawing Sheets

Related U.S. Application Data continuation of application No. 10/970,843, filed on Oct. 20, 2004, now Pat. No. 8,167,944.

(58) Field of Classification Search
CPC ............ A61B 17/7067; A61B 17/7068; A61B 17/7074; A61B 17/7097; A61B 17/70; A61B 17/7062–17/707
See application file for complete search history.

(56) References Cited

U.S. PATENT DOCUMENTS

| | | | |
|---|---|---|---|
| 3,242,120 A | | 3/1966 | Steuber |
| 3,486,505 A | | 12/1969 | Morrison |
| 3,648,691 A | | 3/1972 | Lumb et al. |
| 3,986,383 A | | 10/1976 | Petteys |
| 4,545,374 A | * | 10/1985 | Jacobson ............ A61B 17/0218 600/210 |
| 4,632,101 A | | 12/1986 | Freedland |
| 4,685,447 A | | 8/1987 | Iversen et al. |
| 4,799,484 A | | 1/1989 | Smith et al. |
| 4,863,476 A | | 9/1989 | Shepperd |
| 4,895,564 A | | 1/1990 | Farrell |
| 4,986,831 A | * | 1/1991 | King ........................ A61F 2/062 600/36 |
| 5,011,484 A | * | 4/1991 | Breard ................ A61B 17/7053 606/249 |
| 5,015,247 A | | 5/1991 | Michelson |
| 5,019,081 A | | 5/1991 | Watanabe |
| 5,059,193 A | | 10/1991 | Kuslich |
| 5,092,866 A | | 3/1992 | Breard et al. |
| 5,178,628 A | | 1/1993 | Otsuka et al. |
| 5,180,393 A | | 1/1993 | Commarmond et al. |
| 5,182,281 A | | 1/1993 | Frigola-Constansa et al. |
| 5,188,281 A | | 2/1993 | Fujiwara et al. |
| 5,192,281 A | | 3/1993 | de la Caffiniere |
| 5,195,526 A | | 3/1993 | Michelson |
| 5,298,253 A | | 3/1994 | LeFiles et al. |
| 5,368,594 A | | 11/1994 | Martin et al. |
| 5,390,683 A | | 2/1995 | Pisharodi |
| 5,415,661 A | | 5/1995 | Holmes |
| 5,456,722 A | | 10/1995 | McLeod et al. |
| 5,462,738 A | | 10/1995 | LeFiles et al. |
| 5,472,452 A | | 12/1995 | Trott |
| 5,484,437 A | | 1/1996 | Michelson |
| 5,487,739 A | | 1/1996 | Aebischer et al. |
| 5,489,308 A | | 2/1996 | Kuslich et al. |
| 5,496,318 A | | 3/1996 | Howland et al. |
| 5,531,748 A | | 7/1996 | de la Caffiniere et al. |
| 5,549,679 A | | 8/1996 | Kuslich |
| 5,571,189 A | | 11/1996 | Kuslich |
| 5,591,165 A | | 1/1997 | Jackson |
| 5,609,634 A | | 3/1997 | Voydeville et al. |
| 5,609,636 A | | 3/1997 | Kohrs et al. |
| 5,645,599 A | * | 7/1997 | Samani ...................... A61F 2/44 606/248 |
| 5,654,599 A | | 8/1997 | Casper |
| 5,658,337 A | | 8/1997 | Kohrs et al. |
| 5,674,295 A | | 10/1997 | Ray et al. |
| 5,700,264 A | | 12/1997 | Zucherman et al. |
| 5,725,582 A | | 3/1998 | Bevan et al. |
| 5,741,253 A | | 4/1998 | Michelson |
| 5,762,629 A | | 6/1998 | Kambin |
| 5,836,948 A | | 11/1998 | Zucherman et al. |
| 5,860,977 A | | 1/1999 | Zucherman et al. |
| 5,863,948 A | | 1/1999 | Epstein et al. |
| 5,876,404 A | | 3/1999 | Zucherman et al. |
| RE36,211 E | | 5/1999 | Nonomura et al. |
| 5,904,636 A | | 5/1999 | Chen et al. |
| 5,904,686 A | | 5/1999 | Zucherman et al. |
| 5,928,207 A | | 7/1999 | Pisano et al. |
| 5,948,017 A | * | 9/1999 | Taheri ........................ A61F 2/07 606/194 |
| 5,972,015 A | | 10/1999 | Scribner et al. |
| 6,039,761 A | | 3/2000 | Li et al. |
| 6,045,552 A | | 4/2000 | Zucherman et al. |
| 6,048,342 A | | 4/2000 | Zucherman et al. |
| 6,066,154 A | | 5/2000 | Reiley et al. |
| 6,068,630 A | | 5/2000 | Zucherman et al. |
| 6,074,390 A | | 6/2000 | Zucherman et al. |
| 6,080,155 A | | 6/2000 | Michelson |
| 6,080,157 A | | 6/2000 | Cathro et al. |
| 6,090,112 A | | 7/2000 | Zucherman et al. |
| 6,096,038 A | | 8/2000 | Michelson |
| 6,102,928 A | | 8/2000 | Bonutti |
| D433,193 S | | 10/2000 | Gaw et al. |
| 6,132,464 A | | 10/2000 | Martin et al. |
| 6,149,642 A | | 11/2000 | Gerhart et al. |
| 6,149,652 A | | 11/2000 | Zucherman et al. |
| 6,152,926 A | | 11/2000 | Zucherman et al. |
| 6,156,038 A | | 12/2000 | Zucherman et al. |
| 6,159,215 A | | 12/2000 | Urbahns et al. |
| 6,179,873 B1 | | 1/2001 | Zientek |
| 6,183,471 B1 | | 2/2001 | Zucherman et al. |
| 6,190,387 B1 | | 2/2001 | Zucherman et al. |
| 6,225,048 B1 | | 5/2001 | Soderberg-Naucler et al. |
| 6,235,030 B1 | | 5/2001 | Zucherman et al. |
| 6,238,397 B1 | | 5/2001 | Zucherman et al. |
| 6,264,651 B1 | | 7/2001 | Underwood et al. |
| 6,264,656 B1 | | 7/2001 | Michelson |
| 6,267,765 B1 | | 7/2001 | Taylor et al. |
| 6,270,498 B1 | | 8/2001 | Michelson |
| 6,280,444 B1 | | 8/2001 | Zucherman et al. |
| 6,312,431 B1 | | 11/2001 | Asfora |
| 6,328,730 B1 | | 12/2001 | Harkrider, Jr. |
| 6,332,882 B1 | | 12/2001 | Zucherman et al. |
| 6,332,883 B1 | | 12/2001 | Zucherman et al. |
| 6,336,930 B1 | | 1/2002 | Stalcup et al. |
| 6,348,053 B1 | | 2/2002 | Cachia |
| 6,364,883 B1 | | 4/2002 | Santilli |
| 6,371,989 B1 | | 4/2002 | Chauvin et al. |
| 6,375,682 B1 | | 4/2002 | Fleischmann et al. |
| 6,379,355 B1 | | 4/2002 | Zucherman et al. |
| 6,387,130 B1 | * | 5/2002 | Stone .................... A61F 2/4455 623/17.16 |
| 6,395,032 B1 | | 5/2002 | Gauchet et al. |
| 6,402,740 B1 | | 6/2002 | Ellis et al. |
| 6,402,750 B1 | | 6/2002 | Atkinson et al. |
| 6,402,784 B1 | | 6/2002 | Wardlaw et al. |
| 6,413,228 B1 | | 7/2002 | Hung et al. |
| 6,419,676 B1 | | 7/2002 | Zucherman et al. |
| 6,419,677 B2 | | 7/2002 | Zucherman et al. |
| 6,440,169 B1 | | 8/2002 | Elberg et al. |
| 6,443,988 B2 | | 9/2002 | Felt et al. |
| 6,447,547 B1 | | 9/2002 | Michelson |
| 6,451,019 B1 | | 9/2002 | Zucherman et al. |
| 6,451,020 B1 | | 9/2002 | Zucherman et al. |
| 6,471,976 B1 | | 10/2002 | Taylor et al. |
| 6,478,796 B2 | | 11/2002 | Zucherman et al. |
| 6,478,822 B1 | | 11/2002 | Leroux et al. |
| 6,500,178 B2 | | 12/2002 | Zucherman et al. |
| 6,514,256 B2 | | 2/2003 | Zucherman et al. |
| 6,530,925 B2 | | 3/2003 | Boudard et al. |
| 6,558,333 B2 | | 5/2003 | Gilboa et al. |
| 6,565,570 B2 | | 5/2003 | Sterett et al. |
| 6,572,617 B1 | | 6/2003 | Senegas et al. |
| 6,575,981 B1 | | 6/2003 | Boyd et al. |
| 6,579,319 B2 | | 6/2003 | Goble et al. |
| 6,582,433 B2 | | 6/2003 | Yun |
| 6,582,451 B1 | | 6/2003 | Marucci et al. |
| 6,599,292 B1 | | 7/2003 | Ray |
| 6,610,065 B1 | | 8/2003 | Branch et al. |
| 6,610,091 B1 | | 8/2003 | Reiley |
| 6,626,944 B1 | | 9/2003 | Taylor et al. |
| 6,645,207 B2 | | 11/2003 | Dixon et al. |
| 6,645,211 B2 | | 11/2003 | Magana |
| 6,652,527 B2 | | 11/2003 | Zucherman et al. |
| 6,652,534 B2 | | 11/2003 | Zucherman et al. |
| 6,663,637 B2 | | 12/2003 | Dixon et al. |
| 6,679,886 B2 | | 1/2004 | Weikel et al. |
| 6,695,842 B2 | | 2/2004 | Zucherman et al. |
| 6,699,246 B2 | | 3/2004 | Zucherman et al. |
| 6,699,247 B2 | | 3/2004 | Zucherman et al. |
| 6,702,847 B2 | | 3/2004 | DiCarlo |

(56) References Cited

U.S. PATENT DOCUMENTS

| | | |
|---|---|---|
| 6,712,819 B2 | 3/2004 | Zucherman et al. |
| 6,716,215 B1 | 4/2004 | David et al. |
| 6,716,245 B2 | 4/2004 | Pasquet et al. |
| 6,733,534 B2 | 5/2004 | Sherman |
| 6,746,485 B1 | 6/2004 | Zucherman et al. |
| 6,761,720 B1 | 7/2004 | Senegas et al. |
| 6,783,529 B2 | 8/2004 | Hover et al. |
| 6,783,546 B2 | 8/2004 | Zucherman et al. |
| 6,796,983 B1 * | 9/2004 | Zucherman ........ A61B 17/7065 606/190 |
| 6,835,205 B2 | 12/2004 | Atkinson et al. |
| 6,840,944 B2 | 1/2005 | Suddaby |
| 6,858,029 B2 | 2/2005 | Yeh |
| 6,869,398 B2 | 3/2005 | Obenchain et al. |
| 6,875,212 B2 | 4/2005 | Shaolian et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Arnin et al. |
| 6,974,478 B2 | 12/2005 | Reiley et al. |
| 7,011,685 B2 | 3/2006 | Arnin et al. |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,179,225 B2 * | 2/2007 | Shluzas .............. A61B 17/3439 600/219 |
| 7,187,064 B2 | 3/2007 | Tzu et al. |
| 7,189,234 B2 | 3/2007 | Zucherman et al. |
| 7,189,236 B2 | 3/2007 | Taylor et al. |
| 7,201,751 B2 | 4/2007 | Zucherman et al. |
| 7,217,291 B2 | 5/2007 | Zucherman et al. |
| 7,223,289 B2 | 5/2007 | Trieu et al. |
| 7,229,441 B2 | 6/2007 | Trieu et al. |
| 7,238,204 B2 | 7/2007 | Le Couedic et al. |
| 7,252,673 B2 | 8/2007 | Lim |
| 7,273,496 B2 | 9/2007 | Mitchell |
| 7,282,063 B2 | 10/2007 | Cohen et al. |
| 7,297,162 B2 | 11/2007 | Mujwid |
| 7,306,628 B2 | 12/2007 | Zucherman et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,384,340 B2 | 6/2008 | Eguchi et al. |
| 7,410,501 B2 | 8/2008 | Michelson |
| 7,442,208 B2 | 10/2008 | Mathieu et al. |
| 7,445,637 B2 | 11/2008 | Taylor |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,491,204 B2 | 2/2009 | Marnay et al. |
| 7,503,935 B2 | 3/2009 | Zucherman et al. |
| 7,504,798 B2 | 3/2009 | Kawada et al. |
| 7,510,567 B2 | 3/2009 | Zucherman et al. |
| 7,520,887 B2 | 4/2009 | Maxy et al. |
| 7,520,899 B2 | 4/2009 | Zucherman et al. |
| 7,547,308 B2 | 6/2009 | Bertagnoli et al. |
| 7,549,999 B2 | 6/2009 | Zucherman et al. |
| 7,550,009 B2 | 6/2009 | Arnin et al. |
| 7,565,259 B2 | 7/2009 | Sheng et al. |
| 7,572,276 B2 | 8/2009 | Lim et al. |
| 7,575,600 B2 | 8/2009 | Zucherman et al. |
| 7,585,313 B2 | 9/2009 | Kwak et al. |
| 7,585,316 B2 | 9/2009 | Trieu |
| 7,588,588 B2 | 9/2009 | Spitler et al. |
| 7,591,851 B2 | 9/2009 | Winslow et al. |
| 7,601,170 B2 | 10/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,950 B2 | 12/2009 | Baccelli et al. |
| 7,658,752 B2 | 2/2010 | Labrom et al. |
| 7,662,187 B2 | 2/2010 | Zucherman et al. |
| 7,666,209 B2 | 2/2010 | Zucherman et al. |
| 7,666,228 B2 | 2/2010 | Le Couedic et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,695,513 B2 | 4/2010 | Zucherman et al. |
| 7,699,852 B2 | 4/2010 | Frankel et al. |
| 7,699,873 B2 | 4/2010 | Stevenson et al. |
| 7,727,233 B2 | 6/2010 | Blackwell et al. |
| 7,727,241 B2 | 6/2010 | Gorensek et al. |
| 7,731,751 B2 | 6/2010 | Butler et al. |
| 7,742,795 B2 | 6/2010 | Stone et al. |
| 7,749,231 B2 | 7/2010 | Bonvallet et al. |
| 7,749,252 B2 | 7/2010 | Zucherman et al. |
| 7,749,253 B2 | 7/2010 | Zucherman et al. |
| 7,753,938 B2 | 7/2010 | Aschmann et al. |
| 7,758,619 B2 | 7/2010 | Zucherman et al. |
| 7,758,647 B2 | 7/2010 | Arnin et al. |
| 7,763,028 B2 | 7/2010 | Lim et al. |
| 7,763,050 B2 | 7/2010 | Winslow et al. |
| 7,763,051 B2 | 7/2010 | Labrom et al. |
| 7,763,073 B2 | 7/2010 | Hawkins et al. |
| 7,763,074 B2 | 7/2010 | Altarac et al. |
| 7,766,967 B2 | 8/2010 | Francis |
| 7,776,090 B2 | 8/2010 | Winslow et al. |
| 7,780,709 B2 | 8/2010 | Bruneau et al. |
| 7,789,898 B2 | 9/2010 | Peterman |
| 7,794,476 B2 | 9/2010 | Wisnewski |
| 7,803,190 B2 | 9/2010 | Zucherman et al. |
| 7,806,911 B2 | 10/2010 | Peckham |
| 7,811,308 B2 | 10/2010 | Arnin et al. |
| 7,811,322 B2 | 10/2010 | Arnin et al. |
| 7,811,323 B2 | 10/2010 | Arnin et al. |
| 7,811,324 B2 | 10/2010 | Arnin et al. |
| 7,811,330 B2 | 10/2010 | Arnin et al. |
| 7,819,921 B2 | 10/2010 | Grotz |
| 7,828,822 B2 | 11/2010 | Zucherman et al. |
| 7,828,849 B2 | 11/2010 | Lim |
| 7,833,272 B2 | 11/2010 | Arnin et al. |
| 7,837,688 B2 | 11/2010 | Boyer, II et al. |
| 7,837,711 B2 | 11/2010 | Bruneau et al. |
| 7,837,734 B2 | 11/2010 | Zucherman et al. |
| 7,846,183 B2 | 12/2010 | Blain |
| 7,846,185 B2 | 12/2010 | Carls et al. |
| 7,846,186 B2 | 12/2010 | Taylor |
| 7,857,815 B2 | 12/2010 | Zucherman et al. |
| 7,862,569 B2 | 1/2011 | Zucherman et al. |
| 7,862,586 B2 | 1/2011 | Malek |
| 7,862,590 B2 | 1/2011 | Lim et al. |
| 7,862,592 B2 | 1/2011 | Peterson et al. |
| 7,862,615 B2 | 1/2011 | Carli et al. |
| 7,867,276 B2 | 1/2011 | Matge et al. |
| 7,871,426 B2 | 1/2011 | Chin et al. |
| 7,955,392 B2 | 6/2011 | Dewey et al. |
| 7,985,246 B2 | 7/2011 | Trieu |
| 8,012,207 B2 | 9/2011 | Kim |
| 8,025,684 B2 | 9/2011 | Garcia-Bengochea et al. |
| 8,057,513 B2 | 11/2011 | Kohm et al. |
| 8,062,332 B2 | 11/2011 | Cunningham et al. |
| 8,123,782 B2 | 2/2012 | Altarac et al. |
| 8,123,807 B2 | 2/2012 | Kim |
| 8,128,662 B2 | 3/2012 | Altarac et al. |
| 8,152,837 B2 | 4/2012 | Altarac et al. |
| 8,167,944 B2 | 5/2012 | Kim |
| 8,226,690 B2 | 7/2012 | Altarac et al. |
| 8,273,108 B2 | 9/2012 | Altarac et al. |
| 8,277,488 B2 | 10/2012 | Altarac et al. |
| 8,292,922 B2 | 10/2012 | Altarac et al. |
| 8,317,864 B2 | 11/2012 | Kim |
| 8,409,282 B2 | 4/2013 | Kim |
| 8,425,559 B2 | 4/2013 | Tebbe et al. |

(56) References Cited

U.S. PATENT DOCUMENTS

| | | |
|---|---|---|
| 8,613,747 B2 | 12/2013 | Altarac et al. |
| 8,628,574 B2 | 1/2014 | Altarac et al. |
| 8,740,948 B2 | 6/2014 | Reglos et al. |
| 8,845,726 B2 | 9/2014 | Tebbe et al. |
| 8,864,828 B2 | 10/2014 | Altarac et al. |
| 8,900,271 B2 | 12/2014 | Kim |
| 8,945,183 B2 | 2/2015 | Altarac et al. |
| 9,314,279 B2 | 4/2016 | Kim |
| 9,393,055 B2 | 7/2016 | Altarac et al. |
| 2001/0031965 A1 | 10/2001 | Zucherman et al. |
| 2002/0143331 A1 | 10/2002 | Zucherman et al. |
| 2003/0040746 A1 | 2/2003 | Mitchell et al. |
| 2003/0040753 A1 | 2/2003 | Daum et al. |
| 2003/0074075 A1 | 4/2003 | Thomas et al. |
| 2003/0149438 A1 | 8/2003 | Nichols et al. |
| 2003/0153976 A1 | 8/2003 | Cauthen et al. |
| 2003/0176921 A1 | 9/2003 | Lawson |
| 2003/0220643 A1 | 11/2003 | Ferree |
| 2003/0220650 A1 | 11/2003 | Major et al. |
| 2004/0087947 A1 | 5/2004 | Lim et al. |
| 2004/0106997 A1 | 6/2004 | Lieberson |
| 2004/0106999 A1 | 6/2004 | Mathews |
| 2004/0167625 A1 | 8/2004 | Beyar et al. |
| 2004/0220568 A1 | 11/2004 | Zucherman et al. |
| 2005/0049708 A1 | 3/2005 | Atkinson et al. |
| 2005/0075634 A1 | 4/2005 | Zucherman et al. |
| 2005/0090822 A1 | 4/2005 | DiPoto |
| 2005/0101955 A1 | 5/2005 | Zucherman et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0192586 A1 | 9/2005 | Zucherman et al. |
| 2005/0192671 A1 | 9/2005 | Bao et al. |
| 2005/0209603 A1 | 9/2005 | Zucherman et al. |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228426 A1 | 10/2005 | Campbell |
| 2005/0245937 A1 | 11/2005 | Winslow |
| 2005/0261768 A1* | 11/2005 | Trieu .............. A61B 17/7065 623/17.11 |
| 2005/0278036 A1 | 12/2005 | Leonard et al. |
| 2006/0036258 A1 | 2/2006 | Zucherman et al. |
| 2006/0064165 A1 | 3/2006 | Zucherman et al. |
| 2006/0074431 A1 | 4/2006 | Sutton et al. |
| 2006/0084976 A1 | 4/2006 | Borgstrom et al. |
| 2006/0084983 A1 | 4/2006 | Kim |
| 2006/0084985 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0085074 A1 | 4/2006 | Raiszadeh |
| 2006/0089718 A1 | 4/2006 | Zucherman et al. |
| 2006/0102269 A1 | 5/2006 | Uchida et al. |
| 2006/0122620 A1 | 6/2006 | Kim |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0195102 A1 | 8/2006 | Malandain |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0241597 A1 | 10/2006 | Mitchell et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247773 A1 | 11/2006 | Stamp |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271044 A1 | 11/2006 | Petrini et al. |
| 2006/0271049 A1 | 11/2006 | Zucherman et al. |
| 2006/0271055 A1 | 11/2006 | Thramann |
| 2006/0271061 A1 | 11/2006 | Beyar et al. |
| 2006/0271194 A1 | 11/2006 | Zucherman et al. |
| 2006/0276801 A1 | 12/2006 | Yerby et al. |
| 2006/0276897 A1 | 12/2006 | Winslow et al. |
| 2006/0282077 A1 | 12/2006 | Labrom et al. |
| 2006/0282078 A1 | 12/2006 | Labrom et al. |
| 2007/0016196 A1 | 1/2007 | Winslow et al. |
| 2007/0055237 A1 | 3/2007 | Edidin et al. |
| 2007/0055246 A1 | 3/2007 | Zucherman et al. |
| 2007/0073289 A1 | 3/2007 | Kwak et al. |
| 2007/0100340 A1 | 5/2007 | Lange et al. |
| 2007/0100366 A1 | 5/2007 | Dziedzic et al. |
| 2007/0123863 A1 | 5/2007 | Winslow et al. |
| 2007/0123904 A1 | 5/2007 | Stad et al. |
| 2007/0161991 A1 | 7/2007 | Altarac et al. |
| 2007/0161993 A1 | 7/2007 | Lowery et al. |
| 2007/0173818 A1 | 7/2007 | Hestad et al. |
| 2007/0173821 A1 | 7/2007 | Trieu |
| 2007/0173822 A1 | 7/2007 | Bruneau et al. |
| 2007/0173823 A1 | 7/2007 | Dewey et al. |
| 2007/0173832 A1 | 7/2007 | Tebbe et al. |
| 2007/0173939 A1 | 7/2007 | Kim et al. |
| 2007/0179500 A1 | 8/2007 | Chin et al. |
| 2007/0185490 A1 | 8/2007 | Implicito |
| 2007/0191948 A1 | 8/2007 | Arnin et al. |
| 2007/0191991 A1 | 8/2007 | Addink |
| 2007/0198045 A1 | 8/2007 | Morton et al. |
| 2007/0198091 A1 | 8/2007 | Boyer et al. |
| 2007/0203493 A1 | 8/2007 | Zucherman et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208345 A1 | 9/2007 | Marnay et al. |
| 2007/0208346 A1 | 9/2007 | Marnay et al. |
| 2007/0208366 A1 | 9/2007 | Pellegrino et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquet et al. |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0265626 A1 | 11/2007 | Seme |
| 2007/0270822 A1 | 11/2007 | Heinz |
| 2007/0270823 A1 | 11/2007 | Trieu et al. |
| 2007/0270824 A1 | 11/2007 | Lim et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276372 A1 | 11/2007 | Malandain et al. |
| 2007/0276373 A1 | 11/2007 | Malandain |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2008/0015700 A1 | 1/2008 | Zucherman et al. |

(56) References Cited

U.S. PATENT DOCUMENTS

| | | |
|---|---|---|
| 2008/0021468 A1 | 1/2008 | Zucherman et al. |
| 2008/0021560 A1 | 1/2008 | Zucherman et al. |
| 2008/0021561 A1 | 1/2008 | Zucherman et al. |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0051785 A1 | 2/2008 | Zucherman et al. |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071378 A1 | 3/2008 | Zucherman et al. |
| 2008/0086212 A1 | 4/2008 | Zucherman et al. |
| 2008/0108990 A1 | 5/2008 | Mitchell et al. |
| 2008/0114455 A1 | 5/2008 | Lange et al. |
| 2008/0132952 A1 | 6/2008 | Malandain et al. |
| 2008/0167655 A1 | 7/2008 | Wang et al. |
| 2008/0167656 A1 | 7/2008 | Zucherman et al. |
| 2008/0172057 A1 | 7/2008 | Zucherman et al. |
| 2008/0177272 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0183210 A1 | 7/2008 | Zucherman et al. |
| 2008/0188895 A1 | 8/2008 | Cragg et al. |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234824 A1 | 9/2008 | Youssef et al. |
| 2008/0288075 A1 | 11/2008 | Zucherman et al. |
| 2008/0319550 A1 | 12/2008 | Altarac et al. |
| 2009/0012528 A1 | 1/2009 | Aschmann et al. |
| 2009/0118833 A1 | 5/2009 | Hudgins et al. |
| 2009/0125030 A1 | 5/2009 | Tebbe et al. |
| 2009/0125036 A1 | 5/2009 | Bleich |
| 2009/0138046 A1 | 5/2009 | Altarac et al. |
| 2009/0138055 A1 | 5/2009 | Altarac et al. |
| 2009/0222043 A1 | 9/2009 | Altarac et al. |
| 2009/0248079 A1 | 10/2009 | Kwak et al. |
| 2009/0292315 A1 | 11/2009 | Trieu |
| 2010/0042217 A1 | 2/2010 | Zucherman et al. |
| 2010/0082108 A1 | 4/2010 | Zucherman et al. |
| 2010/0114100 A1 | 5/2010 | Mehdizade |
| 2010/0131009 A1 | 5/2010 | Roebling et al. |
| 2010/0234889 A1 | 9/2010 | Hess |
| 2010/0262243 A1 | 10/2010 | Zucherman et al. |
| 2010/0280551 A1 | 11/2010 | Pool et al. |
| 2010/0305611 A1 | 12/2010 | Zucherman et al. |
| 2011/0313457 A1 | 12/2011 | Reglos et al. |
| 2012/0078301 A1 | 3/2012 | Hess |
| 2012/0158063 A1 | 6/2012 | Altarac et al. |
| 2012/0226315 A1 | 9/2012 | Altarac et al. |
| 2012/0330359 A1 | 12/2012 | Kim |
| 2013/0012998 A1 | 1/2013 | Altarac et al. |
| 2013/0072985 A1 | 3/2013 | Kim |
| 2013/0150886 A1 | 6/2013 | Altarac et al. |
| 2013/0165974 A1 | 6/2013 | Kim |
| 2013/0165975 A1 | 6/2013 | Tebbe et al. |
| 2013/0172932 A1 | 7/2013 | Altarac et al. |
| 2013/0172933 A1 | 7/2013 | Altarac et al. |
| 2013/0289622 A1 | 10/2013 | Kim |
| 2014/0081332 A1 | 3/2014 | Altarac et al. |
| 2014/0214082 A1 | 7/2014 | Reglos et al. |
| 2014/0228884 A1 | 8/2014 | Altarac et al. |
| 2016/0248222 A1 | 8/2016 | Miyata |
| 2016/0317193 A1 | 11/2016 | Kim |
| 2017/0071588 A1 | 3/2017 | Choi et al. |

FOREIGN PATENT DOCUMENTS

| | | |
|---|---|---|
| CN | 101897603 | 12/2010 |
| DE | 69507480 | 9/1999 |
| EP | 322334 | 6/1989 |
| EP | 0767636 | 4/1997 |
| EP | 0768843 B1 | 4/1997 |
| EP | 0959792 B1 | 12/1999 |
| EP | 1027004 A1 | 8/2000 |
| EP | 1030615 A1 | 8/2000 |
| EP | 1138268 | 10/2001 |
| EP | 1330987 A1 | 7/2003 |
| EP | 1056408 B1 | 12/2003 |
| EP | 1343424 B1 | 9/2004 |
| EP | 1454589 A1 | 9/2004 |
| EP | 1148850 B1 | 4/2005 |
| EP | 1299042 B1 | 3/2006 |
| EP | 1578314 B1 | 5/2007 |
| EP | 1675535 B1 | 5/2007 |
| EP | 1861046 A2 | 12/2007 |
| FR | 2681525 A1 | 3/1993 |
| FR | 2722980 A1 | 2/1996 |
| FR | 2816197 A1 | 5/2002 |
| FR | 2884136 A1 | 10/2006 |
| FR | 2888744 A1 | 1/2007 |
| SU | 988281 A1 | 1/1983 |
| WO | WO-9404088 A1 | 3/1994 |
| WO | WO-9426192 A1 | 11/1994 |
| WO | WO-9525485 A1 | 9/1995 |
| WO | WO-9531158 A1 | 11/1995 |
| WO | WO-9600049 A1 | 1/1996 |
| WO | WO-9829047 A1 | 7/1998 |
| WO | WO-9921500 A1 | 5/1999 |
| WO | WO-9921501 A1 | 5/1999 |
| WO | WO-9942051 A1 | 8/1999 |
| WO | WO-0013619 A1 | 3/2000 |
| WO | WO-0044319 A1 | 8/2000 |
| WO | WO-0044321 A2 | 8/2000 |
| WO | WO-0128442 A1 | 4/2001 |
| WO | WO-0191657 A1 | 12/2001 |
| WO | WO-0191658 A1 | 12/2001 |
| WO | WO-0203882 A2 | 1/2002 |
| WO | WO-0207623 A1 | 1/2002 |
| WO | WO-0207624 A1 | 1/2002 |
| WO | WO-02051326 A1 | 7/2002 |
| WO | WO-02067793 A2 | 9/2002 |
| WO | WO-02071960 A1 | 9/2002 |
| WO | WO-02076336 A2 | 10/2002 |
| WO | WO-03007791 A2 | 1/2003 |
| WO | WO-03007829 A1 | 1/2003 |
| WO | WO-03008016 A2 | 1/2003 |
| WO | WO-03015646 A2 | 2/2003 |
| WO | WO-03024298 A2 | 3/2003 |
| WO | WO-03045262 A2 | 6/2003 |
| WO | WO-03099147 A1 | 12/2003 |
| WO | WO-03101350 A1 | 12/2003 |
| WO | WO-04073533 A1 | 9/2004 |
| WO | WO-04110300 A2 | 12/2004 |
| WO | WO-05009300 A1 | 2/2005 |
| WO | WO-05013839 A2 | 2/2005 |
| WO | WO-05025461 A2 | 3/2005 |

(56) References Cited

FOREIGN PATENT DOCUMENTS

| | | |
|---|---|---|
| WO | WO-05041799 A1 | 5/2005 |
| WO | WO-05044152 A1 | 5/2005 |
| WO | WO-05055868 A2 | 6/2005 |
| WO | WO-05079672 A2 | 9/2005 |
| WO | WO-2005086776 A2 | 9/2005 |
| WO | WO-05115261 A1 | 12/2005 |
| WO | WO-06033659 A2 | 3/2006 |
| WO | WO-06034423 A2 | 3/2006 |
| WO | WO-06039243 | 4/2006 |
| WO | WO-06039260 A2 | 4/2006 |
| WO | WO-06045094 A2 | 4/2006 |
| WO | WO-2006045094 A2 | 4/2006 |
| WO | WO-06063047 A2 | 6/2006 |
| WO | WO-06065774 A1 | 6/2006 |
| WO | WO-2006063047 A2 | 6/2006 |
| WO | WO-2006064356 A1 | 6/2006 |
| WO | WO-2006089085 A2 | 8/2006 |
| WO | WO-06102269 A2 | 9/2006 |
| WO | WO-06102428 A1 | 9/2006 |
| WO | WO-06102485 A2 | 9/2006 |
| WO | WO-06107539 A1 | 10/2006 |
| WO | WO-06110462 A2 | 10/2006 |
| WO | WO-06110464 A1 | 10/2006 |
| WO | WO-06110767 A1 | 10/2006 |
| WO | WO-06113080 A2 | 10/2006 |
| WO | WO-06113406 A2 | 10/2006 |
| WO | WO-06113814 A2 | 10/2006 |
| WO | WO-06118945 A1 | 11/2006 |
| WO | WO-06119235 A1 | 11/2006 |
| WO | WO-06119236 A2 | 11/2006 |
| WO | WO-06135511 A1 | 12/2006 |
| WO | WO-07015028 A1 | 2/2007 |
| WO | WO-07035120 A1 | 3/2007 |
| WO | WO-07075375 A2 | 7/2007 |
| WO | WO-07075791 A2 | 7/2007 |
| WO | WO-07089605 A2 | 8/2007 |
| WO | WO-07089905 A2 | 8/2007 |
| WO | WO-07089975 A1 | 8/2007 |
| WO | WO-07097735 A2 | 8/2007 |
| WO | WO-07109402 A2 | 9/2007 |
| WO | WO-07110604 A1 | 10/2007 |
| WO | WO-07111795 A1 | 10/2007 |
| WO | WO-07111979 A2 | 10/2007 |
| WO | WO-07111999 A2 | 10/2007 |
| WO | WO-07117882 A1 | 10/2007 |
| WO | WO-07121070 A2 | 10/2007 |
| WO | WO-07127550 A2 | 11/2007 |
| WO | WO-07127588 A1 | 11/2007 |
| WO | WO-07127677 A1 | 11/2007 |
| WO | WO-07127689 A2 | 11/2007 |
| WO | WO-07127694 A2 | 11/2007 |
| WO | WO-07127734 A2 | 11/2007 |
| WO | WO-07127736 A2 | 11/2007 |
| WO | WO-07131165 A2 | 11/2007 |
| WO | WO-07134113 A2 | 11/2007 |
| WO | WO-2008009049 A1 | 1/2008 |
| WO | WO-08048645 A2 | 4/2008 |
| WO | WO-2008057506 A2 | 5/2008 |
| WO | WO-2008130564 A1 | 10/2008 |
| WO | WO-2009014728 A2 | 1/2009 |
| WO | WO-2009033093 A1 | 3/2009 |
| WO | WO-2009086010 A2 | 7/2009 |
| WO | WO-2009091922 A2 | 7/2009 |
| WO | WO-2009094463 A2 | 7/2009 |
| WO | WO-2009114479 A2 | 9/2009 |
| WO | WO-2011084477 A2 | 7/2011 |

OTHER PUBLICATIONS

International Search Report and Written Opinion; Application No. PCT/US2005/038026; dated Apr. 22, 2008, 9 pages.
International Search Report and Written Opinion; Application No. PCT/US2005/044256; dated Jul. 28, 2006, 7 pages.
International Search Report and Written Opinion; Application No. PCT/US2006/047824; dated Oct. 16, 2008, 17 pages.
International Search Report and Written Opinion; Application No. PCT/US2006/048611; dated Oct. 14, 2008; 10 pages.
International Search Report and Written Opinion; Application No. PCT/US2006/048614; dated Feb. 3, 2006; 23 pages.
International Search Report and Written Opinion; Application No. PCT/US2007/022171; dated Apr. 15, 2008, 9 pages.
International Search Report and Written Opinion; Application No. PCT/US2007/023312; dated May 22, 2008, 14 pages.
International Search Report and Written Opinion; Application No. PCT/US2008/004901; dated Aug. 19, 2008, 7 pages.
International Search Report and Written Opinion; Application No. PCT/US2008/008382; dated Mar. 2, 2009, 13 pages.
International Search Report and Written Opinion; Application No. PCT/US2008/008983; dated Feb. 23, 2009, 7 pages.
International Search Report and Written Opinion; Application No. PCT/US2008/075487; dated Dec. 31, 2008, 7 pages.
International Search Report and Written Opinion; Application No. PCT/US2008/087527; dated Jul. 30, 2009, 10 pages.
International Search Report and Written Opinion; Application No. PCT/US2009/031150; dated Aug. 28, 2009, 6 pages.
International Search Report and Written Opinion; Application No. PCT/US2009/031710; dated Sep. 1, 2009, 10 pages.
International Search Report and Written Opinion; Application No. PCT/US2009/036561; dated Sep. 17, 2009, 12 pages.
Minns, R.J., et al., "Preliminary Design and Experimental Studies of a Noval Soft Implant for Correcting Sagittal Plane Instability in the Lumbar Spine," (1997) Spine, 22(16): 1819-1827.
Supplementary European Search Report; Application No. EP05849654.6; Applicant: Vertiflex, Inc.; dated May 15, 2009, 10 pages.
Supplementary European Search Report; Application No. EP07861426.0; Applicant: Vertiflex, Inc.; dated Jun. 7, 2011, 6 pages.
Supplementary European Search Report; Application No. EP07861721.4; Applicant: Vertiflex, Inc.; dated Nov. 24, 2009, 6 pages.
Supplementary European Search Report; Application No. EP09170304.1; Applicant: Vertiflex, Inc.; dated Nov. 11, 2009, 5 pages.
Supplementary European Search Report; Application No. EP09170338.9; Applicant: Vertiflex, Inc.; dated Nov. 12, 2009, 6 pages.
Supplementary European Search Report; Application No. EP09702116.6; Applicant: Vertiflex, Inc.; dated Feb. 11, 2011, 6 pages.
Supplementary European Search Report; Application No. EP11151901.3; Applicant: Vertiflex, Inc.; dated Apr. 7, 2011, 6 pages.
Swan, Colby, "Preliminary Design and Experimental Studies of a Novel Soft Implant for Correcting Sogittal Plane Instability in the Lumbar Spine," Spine, 1997, 22(16), 1826-1827.
Supplementary European Search Report; Application No. EP05815519.3; Applicant: The Board of Trustees of Leland Stanford Junior University; dated Sep. 28, 2011, 9 pages.
Supplementary European Search Report; Application No. EP05849654; Applicant: The Board of Trustees of Leland Stanford Junior University; dated May 15, 2009, 5 pages.
Australia Exam Report for Application No. AU2006329867, Applicant: The Board of Trustees of Leland Stanford Junior University; dated Jan. 27, 2012, 2 pages.
Australia Exam Report for Application No. AU2007317886, Applicant: VertiFlex, Inc.; dated Jun. 18, 2012, 3 pages.
Australia Exam Report for Application No. AU2008241447, Applicant: VertiFlex, Inc.; dated Jul. 5, 2012, 4 pages.
Australia Exam Report for Application No. AU2008275708, Applicant: VertiFlex, Inc.; dated Nov. 12, 2012, 4 pages.
Australia Exam Report for Application No. AU2008279680, Applicant: VertiFlex, Inc.; dated Oct. 30, 2012, 5 pages.
Australia Exam Report for Application No. AU2008296066, Applicant: VertiFlex, Inc.; dated Mar. 6, 2013, 3 pages.

(56) References Cited

OTHER PUBLICATIONS

Australia Exam Report for Application No. AU2008343092, Applicant: VertiFlex, Inc.; dated Feb. 8, 2013, 4 pages.
Australia Exam Report No. 2 for Application No. AU2009206098, Applicant: VertiFlex, Inc.; dated Aug. 19, 2014, 4 pages.
Australia Exam Report No. 1 for Application No. AU2009206098, Applicant: VertiFlex, Inc.; dated Mar. 6, 2013, 4 pages.
Canada Exam Report for Application No. CA2634251, Applicant: The Board of Trustees of Leland Stanford Junior University; dated Dec. 3, 2013, 2 pages.
Canada Exam Report for Application No. CA2668833, Applicant: Vertiflex, Inc.; dated Dec. 5, 2013, 2 pages.
Canada Exam Report for Application No. CA2695937, Applicant: Vertiflex, Inc.; dated Aug. 7, 2014, 2 pages.
Canada Exam Report for Application No. CA2697628, Applicant: Vertiflex, Inc.; dated Oct. 16, 2014, 2 pages.
Canada Exam Report for Application No. CA2698718, Applicant: Vertiflex, Inc.; dated May 20, 2014, 3 pages.
Supplementary European Search Report; Application No. EP06845480; Applicant: VertiFlex, Inc.; dated Aug. 14, 2012, 9 pages.
Supplementary European Search Report for Application No. EP13184922.6; Applicant: VertiFlex, Inc.; dated Oct. 30, 2013, 8 pages.
Supplementary European Search Report for Application No. EP07861426; Applicant: VertiFlex, Inc.; dated Jun. 7, 2011, 6 pages.
Supplementary European Search Report for Application No. EP07861721.4; Applicant: VertiFlex, Inc.; dated Nov. 24, 2009, 6 pages.
Supplementary European Search Report for Application No. EP09170304.1; Applicant: VertiFlex, Inc.; dated Nov. 24, 2009, 5 pages.
Supplementary European Search Report for Application No. EP09170338.9; Applicant: VertiFlex, Inc.; dated Nov. 24, 2009, 6 pages.
Supplementary European Search Report for Application No. EP11151901.3; Applicant: VertiFlex, Inc.; dated Apr. 7, 2011, 6 pages.
Supplementary European Search Report for Application No. EP08742949.4; Applicant: VertiFlex, Inc.; dated Sep. 17, 2012, 6 pages.
Supplementary European Search Report for Application No. EP08780034.8; Applicant: VertiFlex, Inc.; dated Sep. 19, 2012, 7 pages.
Supplementary European Search Report for Application No. EP08794704.0; Applicant: VertiFlex, Inc.; dated Oct. 23, 2012, 9 pages.
Supplementary European Search Report for Application No. EP08799267.3; Applicant: VertiFlex, Inc.; dated Jun. 29, 2011, 7 pages.
Supplementary European Search Report for Application No. EP08867282.9; Applicant: VertiFlex, Inc.; dated Nov. 28, 2012, 10 pages.
Supplementary European Search Report for Application No. EP09702116.6; Applicant: VertiFlex, Inc.; dated Feb. 11, 2011, 7 pages.
International Search Report and Written Opinion; Application No. PCT/US2010/060498; dated Aug. 25, 2011, 17 pages.
Australia Exam Report for Application No. AU2009223607, Applicant: VertiFlex, Inc.; dated Jun. 4, 2013, 3 pages.
ASNR Neuroradiology Patient Information website, Brain and Spine Imaging: A Patient's Guide to Neuroradiology; Myelography; http://www.asnr.org/patientinfo/procedures/myelography.shtml#sthash.sXIDOxWq.dpbs, Copyright 2012-2013.
European Search Report Application No. EP05815519.3; Applicant: The Board of Trustees of the Leland Stanford Junior University; dated Mar. 2, 2016, 4 pages.

* cited by examiner

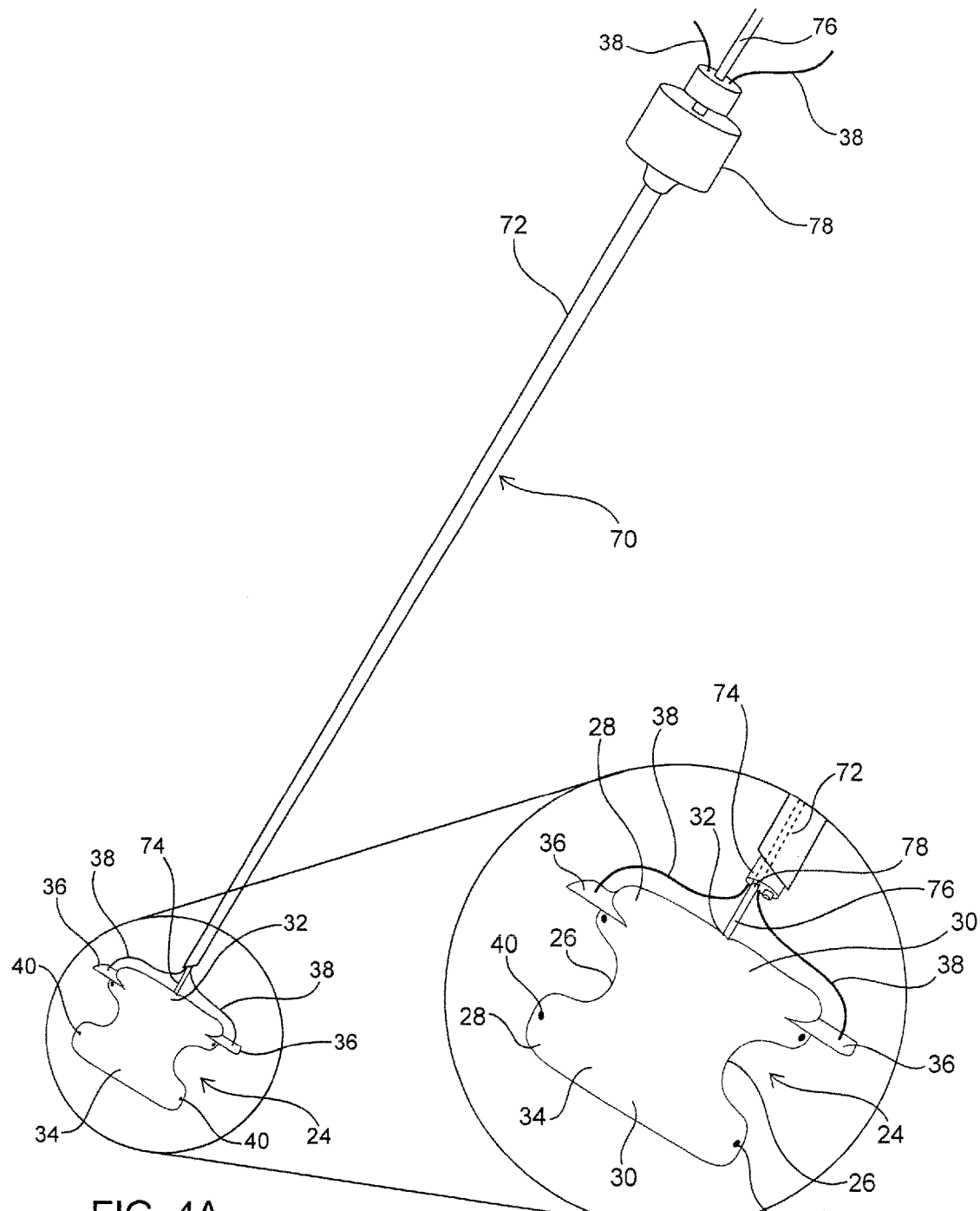

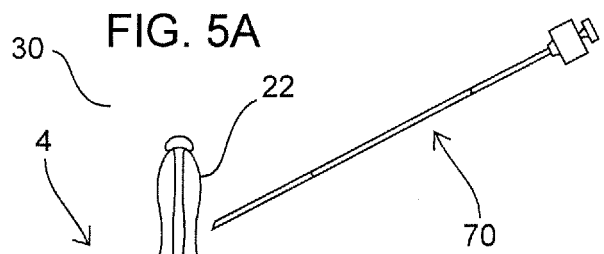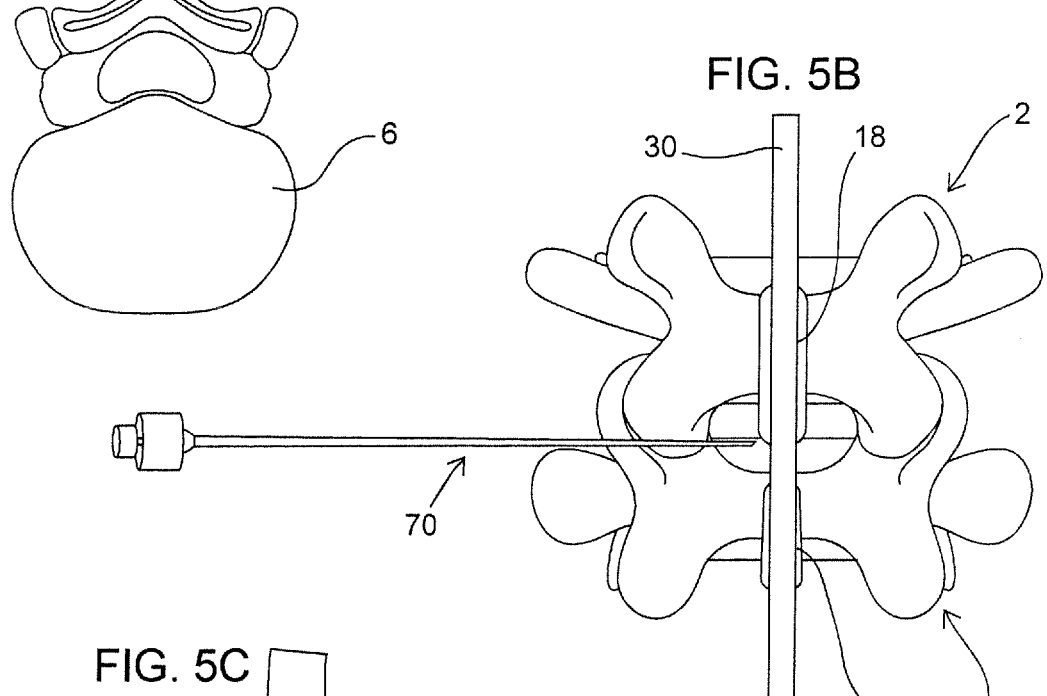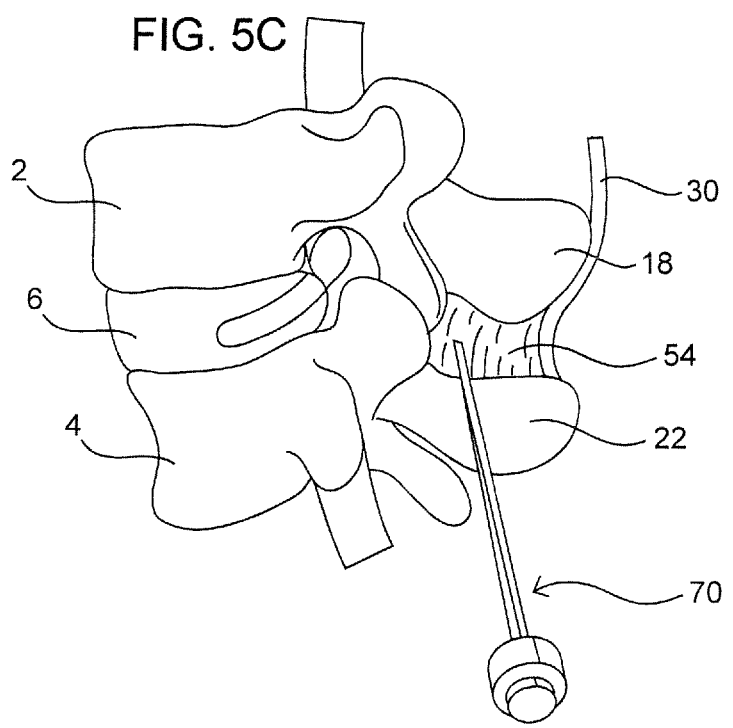

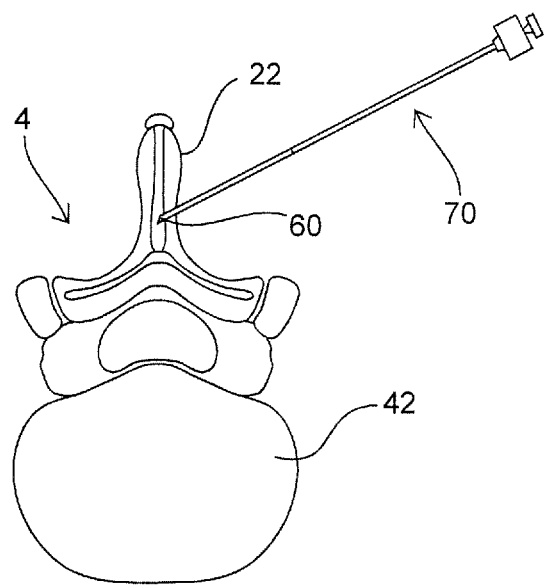
FIG. 6A
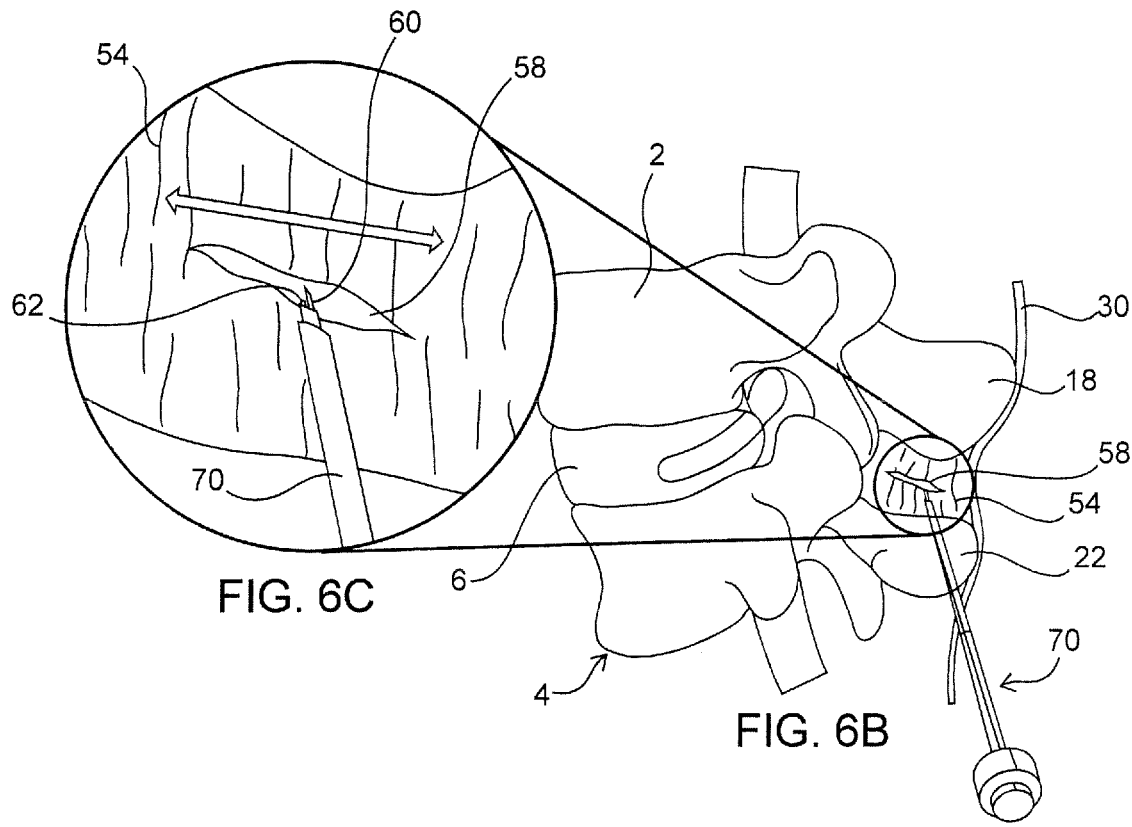
FIG. 6C
FIG. 6B

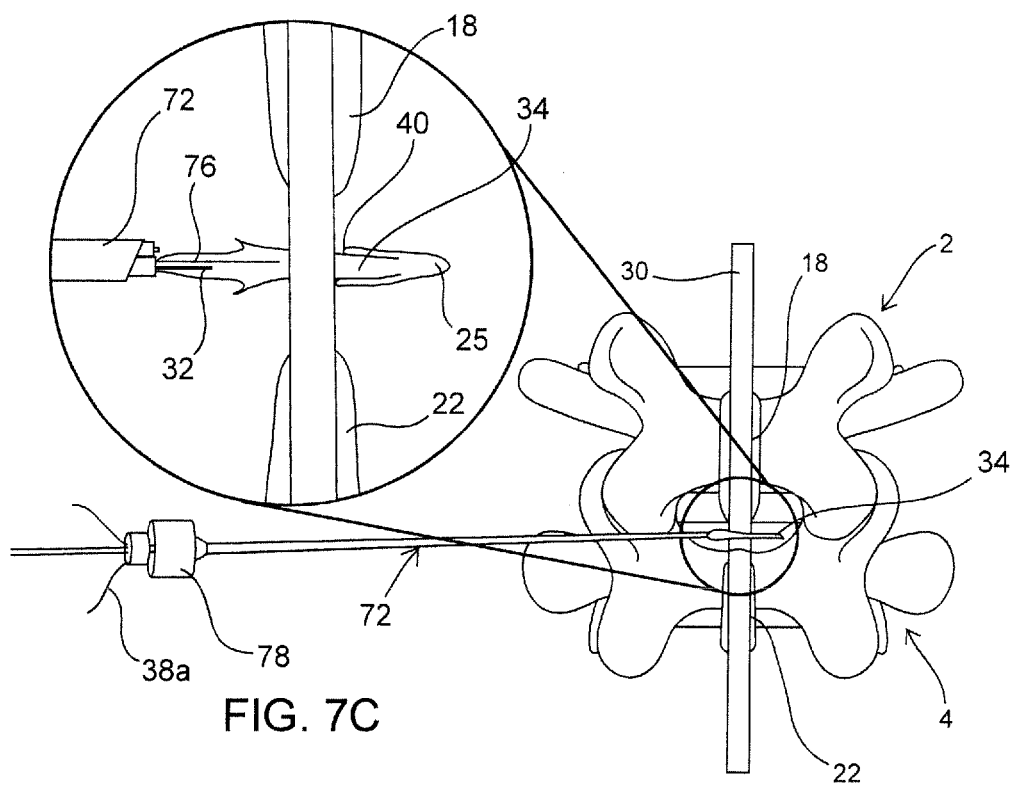
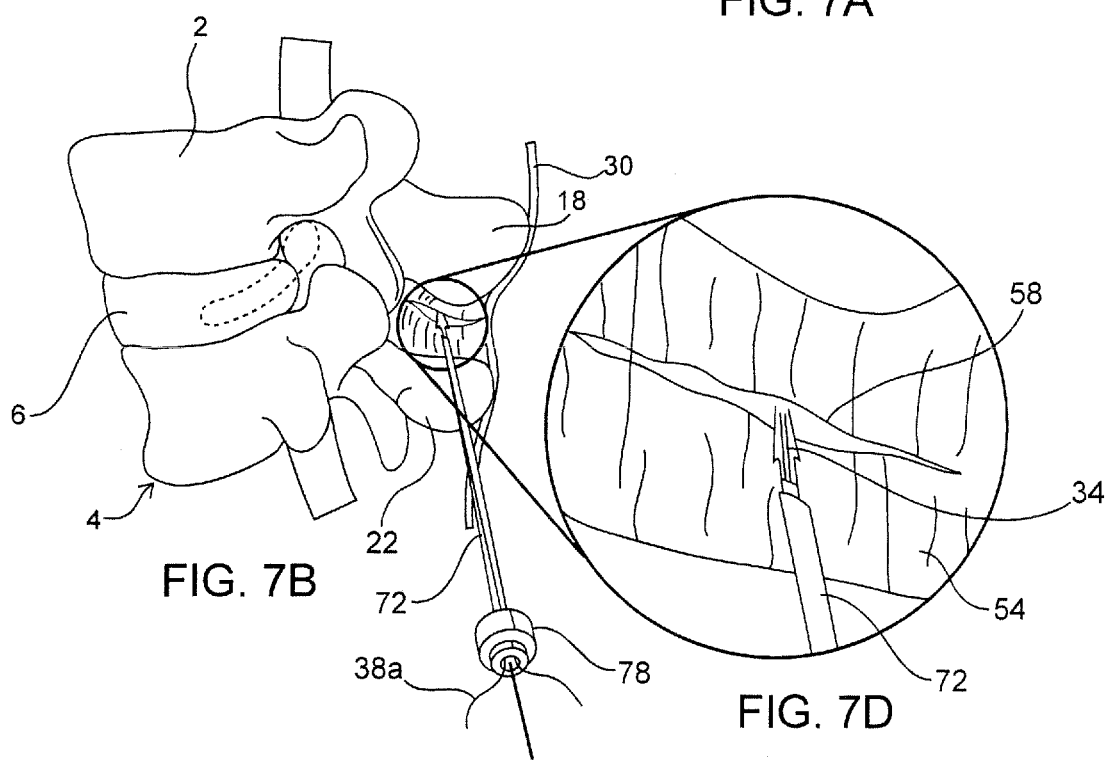

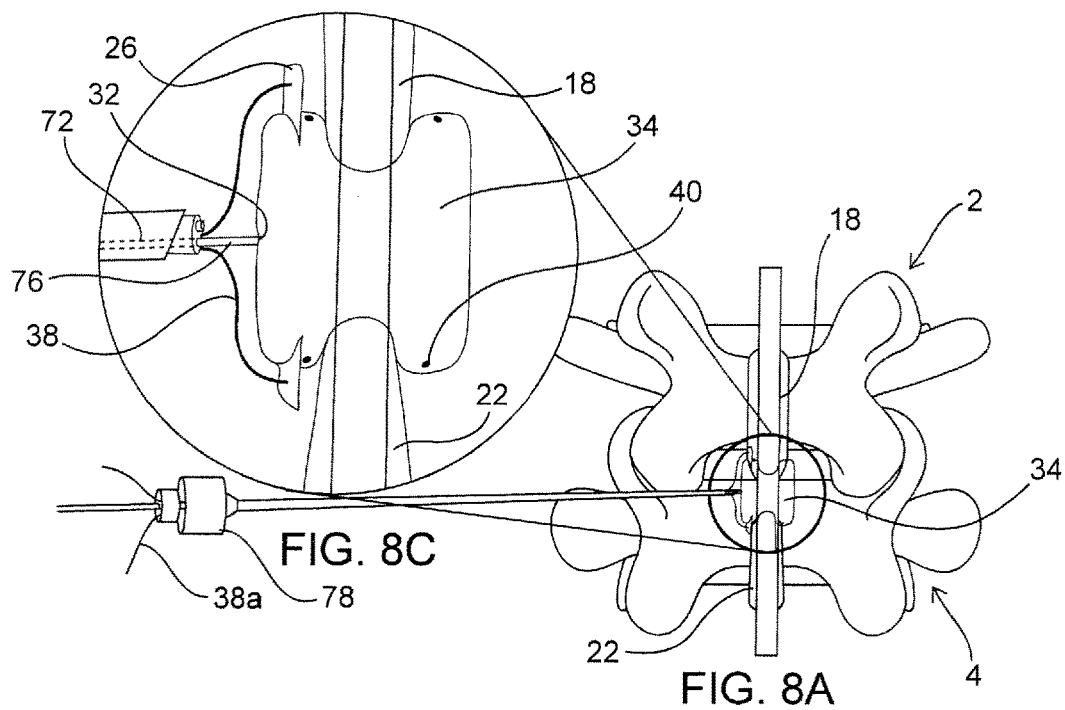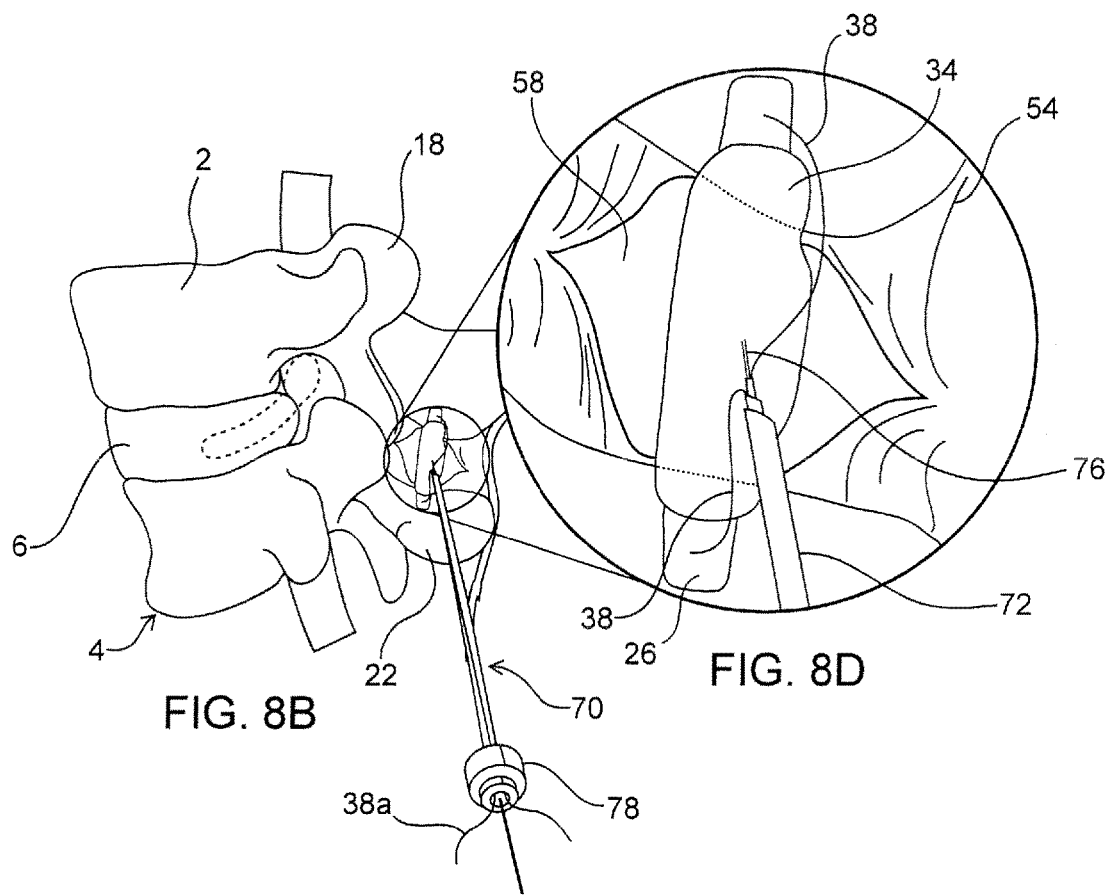

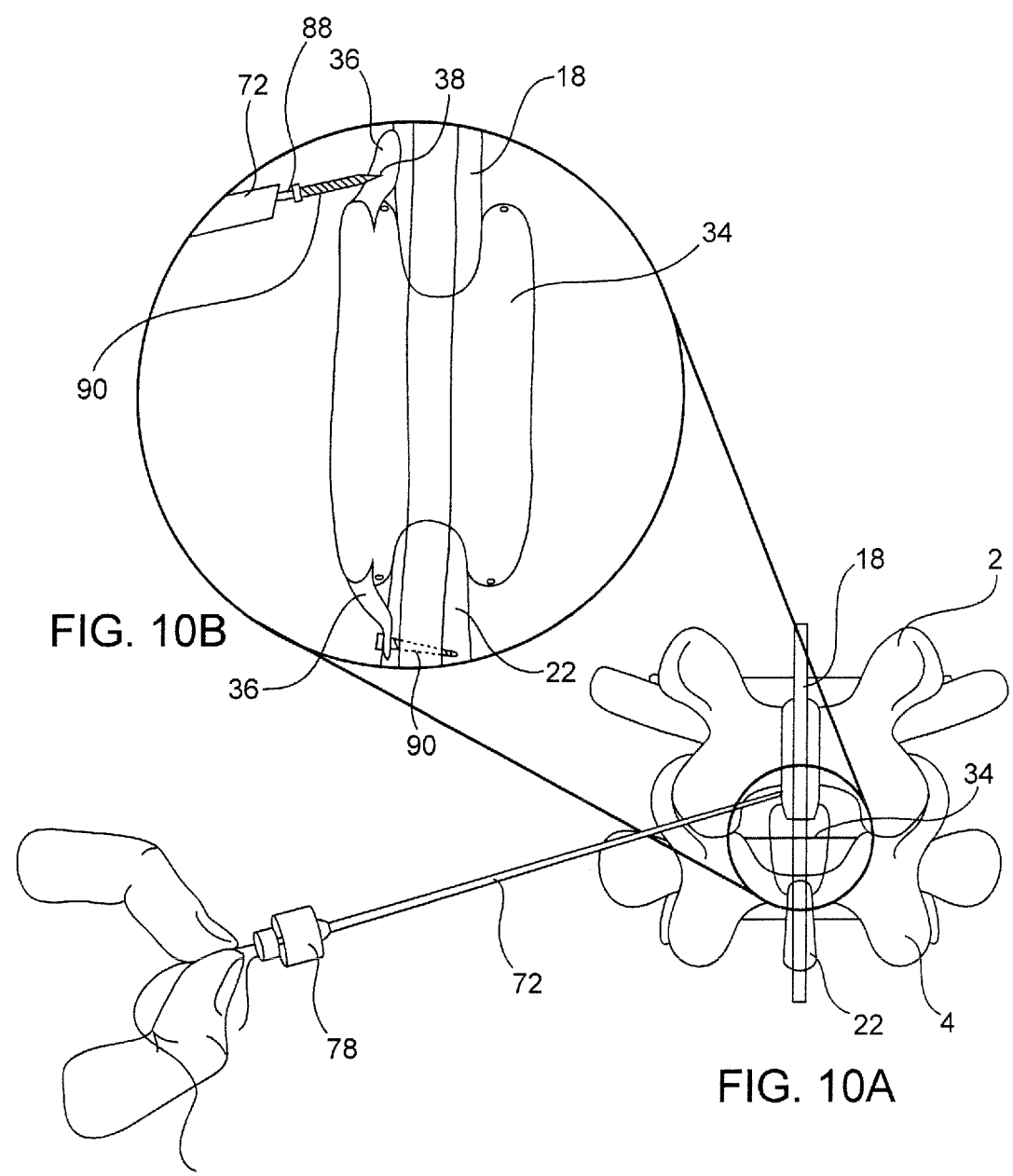

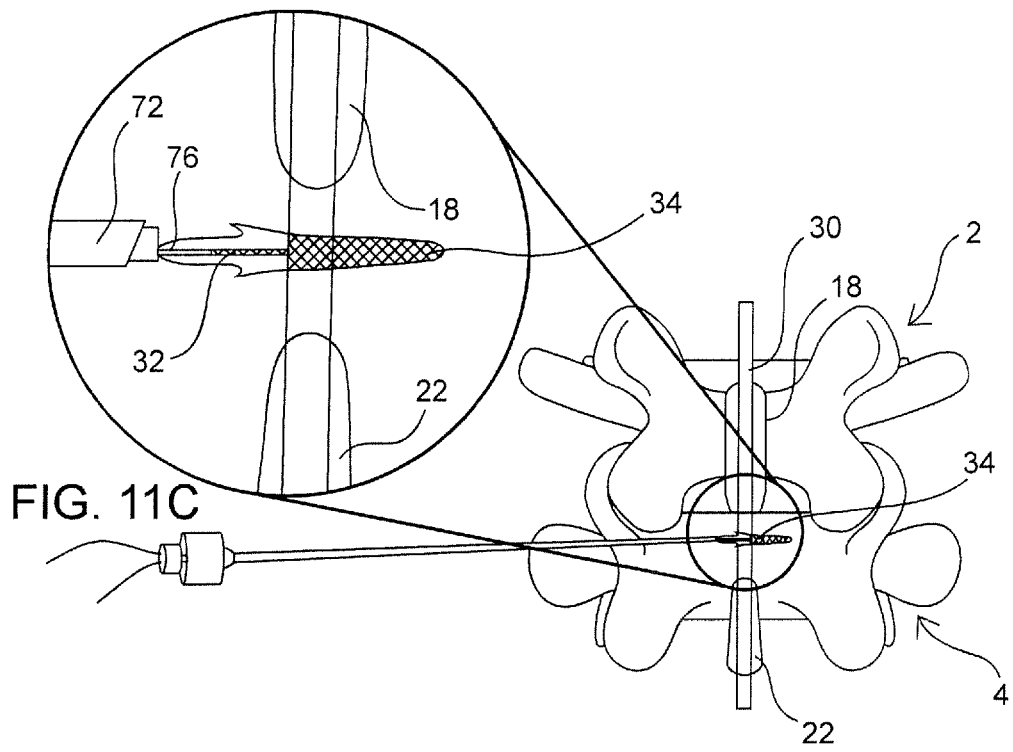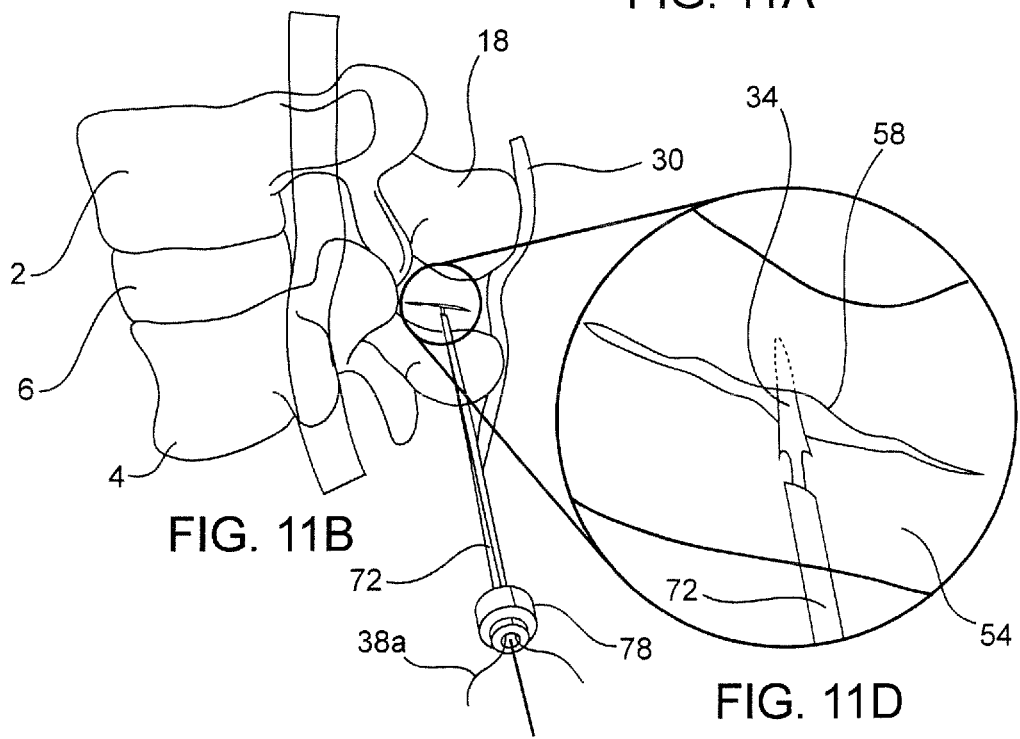

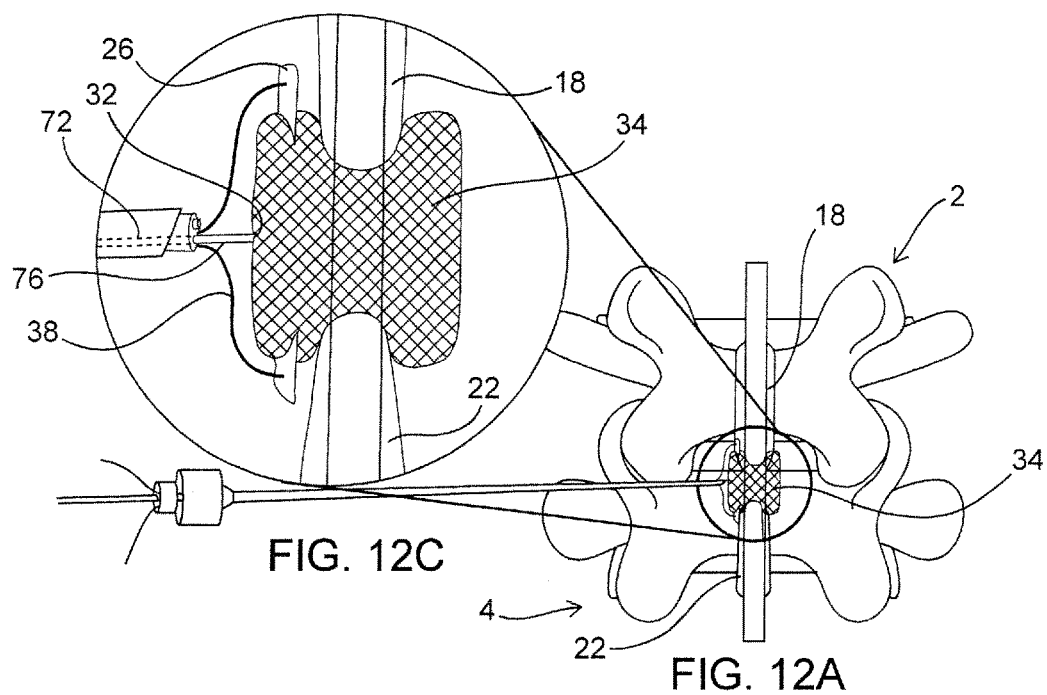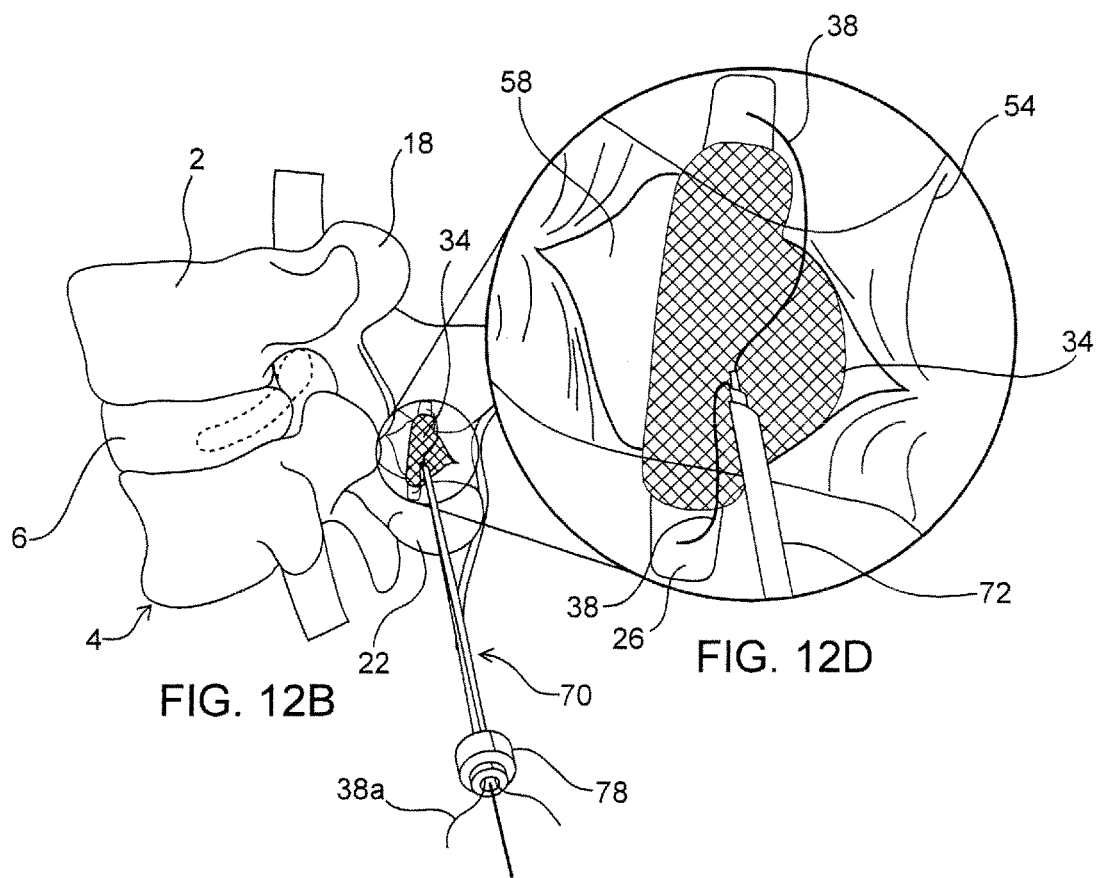

SYSTEMS AND METHODS FOR POSTERIOR DYNAMIC STABILIZATION OF THE SPINE

This application is a continuation of U.S. patent application Ser. No. 13/461,026, filed on May 1, 2012, now U.S. Pat. No. 8,900,271, and entitled "SYSTEMS AND METHODS FOR POSTERIOR DYNAMIC STABILIZATION OF THE SPINE," which is a continuation of U.S. patent application Ser. No. 10/970,843, filed on Oct. 20, 2004, now U.S. Pat. No. 8,167,944, and entitled "SYSTEMS AND METHODS FOR POSTERIOR DYNAMIC STABILIZATION OF THE SPINE." Each of these applications is hereby incorporated by reference in its entirety.

FIELD OF THE INVENTION

The present invention is directed towards the treatment of spinal disorders and pain. More particularly, the present invention is directed to systems and methods of treating the spine, which eliminate pain and enable spinal motion, which effectively mimics that of a normally functioning spine.

BACKGROUND OF THE INVENTION

FIG. 1 illustrates a portion of the human spine having a superior vertebra 2 and an inferior vertebra 4, with an intervertebral disc 6 located in between the two vertebral bodies. The superior vertebra 2 has superior facet joints 8a and 8b, inferior facet joints 10a and 10b, posterior arch 16 and spinous process 18. Pedicles 3a and 3b interconnect the respective superior facet joints 8a, 8b to the vertebral body 2. Extending laterally from superior facet joints 8a, 8b are transverse processes 7a and 7b, respectively. Extending between each inferior facet joints 10a and 10b and the spinous process 18 are lamina 5a and 5b, respectively. Similarly, inferior vertebra 4 has superior facet joints 12a and 12b, superior pedicles 9a and 9b, transverse processes 11a and 11b, inferior facet joints 14a and 14b, lamina 15a and 15b, posterior arch 20, spinous process 22.

The superior vertebra with its inferior facets, the inferior vertebra with its superior facet joints, the intervertebral disc, and seven spinal ligaments (not shown) extending between the superior and inferior vertebrae together comprise a spinal motion segment or functional spine unit. Each spinal motion segment enables motion along three orthogonal axes, both in rotation and in translation. The various spinal motions are illustrated in FIGS. 2A-2C. In particular, FIG. 2A illustrates flexion and extension motions and axial loading, FIG. 2B illustrates lateral bending motion and FIG. 2C illustrated axial rotational motion. A normally functioning spinal motion segment provides physiological limits and stiffness in each rotational and translational direction to create a stable and strong column structure to support physiological loads.

Traumatic, inflammatory, metabolic, synovial, neoplastic and degenerative disorders of the spine can produce debilitating pain that can affect a spinal motion segment's ability to properly function. The specific location or source of spinal pain is most often an affected intervertebral disc or facet joint. Often, a disorder in one location or spinal component can lead to eventual deterioration or disorder, and ultimately, pain in the other.

Spine fusion (arthrodesis) is a procedure in which two or more adjacent vertebral bodies are fused together. It is one of the most common approaches to alleviating various types of spinal pain, particularly pain associated with one or more affected intervertebral discs. While spine fusion generally helps to eliminate certain types of pain, it has been shown to decrease function by limiting the range of motion for patients in flexion, extension, rotation and lateral bending. Furthermore, the fusion creates increased stresses on adjacent non-fused motion segments and accelerated degeneration of the motion segments. Additionally, pseudarthrosis (resulting from an incomplete or ineffective fusion) may not provide the expected pain-relief for the patient. Also, the device(s) used for fusion, whether artificial or biological, may migrate out of the fusion site creating significant new problems for the patient.

Various technologies and approaches have been developed to treat spinal pain without fusion in order to maintain or recreate the natural biomechanics of the spine. To this end, significant efforts are being made in the use of implantable artificial intervertebral discs. Artificial discs are intended to restore articulation between vertebral bodies so as to recreate the full range of motion normally allowed by the elastic properties of the natural disc. Unfortunately, the currently available artificial discs do not adequately address all of the mechanics of motion for the spinal column.

It has been found that the facet joints can also be a significant source of spinal disorders and debilitating pain. For example, a patient may suffer from arthritic facet joints, severe facet joint tropism, otherwise deformed facet joints, facet joint injuries, etc. These disorders lead to spinal stenosis, degenerative spondylolithesis, and/or isthmic spondylotlisthesis, pinching the nerves that extend between the affected vertebrae.

Current interventions for the treatment of facet joint disorders have not been found to provide completely successful results. Facetectomy (removal of the facet joints) may provide some pain relief; but as the facet joints help to support axial, torsional, and shear loads that act on the spinal column in addition to providing a sliding articulation and mechanism for load transmission, their removal inhibits natural spinal function. Laminectomy (removal of the lamina, including the spinal arch and the spinous process) may also provide pain relief associated with facet joint disorders; however, the spine is made less stable and subject to hypermobility. Problems with the facet joints can also complicate treatments associated with other portions of the spine. In fact, contraindications for disc replacement, include arthritic facet joints, absent facet joints, severe facet joint tropism, or otherwise deformed facet joints due to the inability of the artificial disc (when used with compromised or missing facet joints) to properly restore the natural biomechanics of the spinal motion segment.

While various attempts have been made at facet joint replacement, they have been inadequate. This is due to the fact that prosthetic facet joints preserve existing bony structures and therefore do not address pathologies that affect facet joints themselves. Certain facet joint prostheses, such as those disclosed in U.S. Pat. No. 6,132,464, are intended to be supported on the lamina or the posterior arch. As the lamina is a very complex and highly variable anatomical structure, it is very difficult to design a prosthesis that provides reproducible positioning against the lamina to correctly locate the prosthetic facet joints. In addition, when facet joint replacement involves complete removal and replacement of the natural facet joint, as disclosed in U.S. Pat. No. 6,579,319, the prosthesis is unlikely to endure the loads and cycling experienced by the vertebra. Thus, the facet joint replacement may be subject to long-term displacement. Furthermore, when facet joint disorders are accompanied by disease or trauma to other structures of a vertebra (such as the lamina, spinous process, and/or transverse processes) facet joint replacement is insufficient to treat the problem(s).

Most recently, surgical-based technologies, referred to as "dynamic posterior stabilization," have been developed to address spinal pain resulting from more than one disorder, when more than one structure of the spine have been compromised. An objective of such technologies is to provide the support of fusion-based implants while maximizing the natural biomechanics of the spine. Dynamic posterior stabilization systems typically fall into one of two general categories: posterior pedicle screw-based systems and interspinous spacers.

Examples of pedicle screw-based systems are disclosed in U.S. Pat. Nos. 5,015,247, 5,484,437, 5,489,308, 5,609,636 and 5,658,337, 5,741,253, 6,080,155, 6,096,038, 6,264,656 and 6,270,498. These types of systems involve the use of screws that are positioned in the vertebral body through the pedicle. Certain types of these pedicle screw-based systems may be used to augment compromised facet joints, while others require removal of the spinous process and/or the facet joints for implantation. One such system, the Zimmer Spine Dyncsys® employs a cord which is extended between the pedicle screws and a fairly rigid spacer which is passed over the cord and positioned between the screws. While this system is able to provide load sharing and restoration of disc height, because it is so rigid, it does not effective in preserving the natural motion of the spinal segment into which it is implanted. Other pedicle screw-based systems employ articulating joints between the pedicle screws. Because these types of systems require the use of pedicle screws, implantation of the systems are often more invasive to implant than interspinous spacers.

Where the level of disability or pain to the affected spinal motion segments is not that severe or where the condition, such as an injury, is not chronic, the use of interspinous spacers are preferred over pedicle based systems as they require a less invasive implantation approach and less dissection of the surrounding tissue and ligaments. Examples of interspinous spacers are disclosed in U.S. Pat. Nos. Re. 36,211, 5,645,599, 6,695,842, 6,716,245 and 6,761,720. The spacers, which are made of either a hard or compliant material, are placed between adjacent spinous processes. The harder material spacers are fixed in place by means of the opposing force caused by distracting the affected spinal segment and/or by use of keels that anchor into the spinous process. The more compliant or flexible spacers employ artificial ligaments that are wrapped around the spinous processes of the vertebrae above and below the level where the spacer is implanted. While slightly less invasive than the procedure required for implanting a pedicle screw-based dynamic stabilization system, the implantation of interspinous spacers still require muscle and supraspinous and interspinous ligament dissection.

With the limitations of current spine stabilization technologies, there is clearly a need for an improved means and method for dynamic posterior stabilization of the spine that address the drawbacks of prior devices. In particular, it would be highly beneficial to have a dynamic stabilization system that involves a minimally invasive implantation procedure, where the extent of distraction between the affected vertebrae is adjustable upon implantation and at a later time if necessary. It would be additionally advantageous if the system or device was also removable in a minimally invasive manner.

SUMMARY OF THE INVENTION

The present invention provides devices, systems and methods for stabilizing at least one spinal motion segment. The devices include an expandable spacer or member having an unexpanded configuration and an expanded configuration, wherein the expandable member in an expanded configuration has a size, volume and/or shape configured for positioning between the spinous processes of adjacent vertebrae in order to distract the vertebrae relative to each other. The expandable member may be balloon made of either non-compliant or compliant material, or may include a mesh material which may be coated or lined with a non-porous material. The device may further include a port for coupling to a source of an inflation and/or expansion medium for inflating and/or expanding the expandable member. In certain embodiments, the port may be used to deflate or evacuate the expandable member. The devices may further include one or more tabs for anchoring the expandable member to the spinous processes. Optionally, the device may include one marker on a surface of the expandable member to facilitate fluoroscopic imaging.

The invention further includes systems for stabilizing at least one spinal motion segment which include one or more expandable members and an expansion medium for injection within or for filling the interior of the expandable member via the port. The subject systems may further include at least one means for anchoring or securing the expandable member to the spinal motion segment.

The invention further includes methods for stabilizing at least one spinal motion segment which involve the implantation of one or more devices or expandable spacers of the present invention, in which the expandable member is positioned between the spinous processes of adjacent vertebrae in an unexpanded condition and then subsequently expanded to a size and/or shape for selectively distracting the adjacent vertebrae. The invention also contemplates the temporary implantation of the subject devices which may be subsequently removed from the patient once the intended treatment is complete. Many of the methods involve the percutaneous implantation of the subject devices.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 4A illustrates an interspinous device of the present invention in an expanded state coupled to a cannula of the delivery system of the present invention. FIG. 4B is an enlarged view of the interspinous device of FIG. 4A.

FIGS. 5A-5C illustrates top, dorsal and side views of an initial step of the method of the present invention in which a cannula is delivered to the target implant site.

FIGS. 6A and 6B illustrate dorsal and side views of the step of dissecting an opening within the spinous ligament utilizing a cutting instrument of the system of FIGS. 3 and 4. FIG. 6C is an enlarged view of the target area within the spinous ligament.

FIGS. 7A and 7B illustrate dorsal aid side views of the step of inserting the interspinous device of FIG. 4A into the dissected opening of the spinous ligament. FIGS. 7C and 7D are enlarged views of the target area in FIGS. 7A and 7B, respectively.

FIGS. 8A and 8B illustrate dorsal aid side views of the step of inflating or expanding the interspinous device of FIG. 4A within the implant site. FIGS. 8C and 8D are enlarged views of the target area in FIGS. 8C and 8D, respectively.

FIG. 10A illustrates a dorsal view of the step of further securing the interspinous device of FIG. 4A within the implant site. FIG. 10B is an enlarged view of the target area in FIG. 10A.

FIGS. 11A and 11B illustrate dorsal aid side views of the step of inserting another embodiment of an interspinous device into the dissected opening of the spinous ligament. FIGS. 11C and 11D are enlarged views of the target area in FIGS. 11A and 11B, respectively.

FIGS. 12A and 12B illustrate dorsal aid side views of the step of expanding the interspinous device of FIGS. 11A-11D within the implant site. FIGS. 12C and 12D are enlarged views of the target area in FIGS. 12A and 12B, respectively.

DETAILED DESCRIPTION OF THE INVENTION

Figure 1:
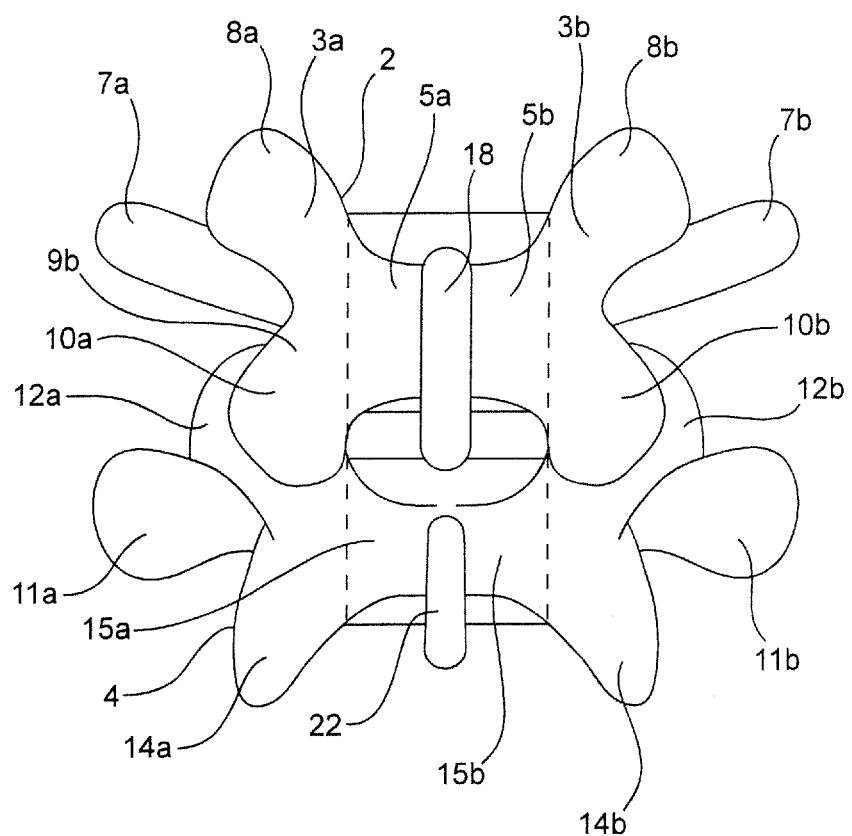
FIG. 1 illustrated s perspective view of a portion of the human spine having two vertebral segments.
Figure 2A:
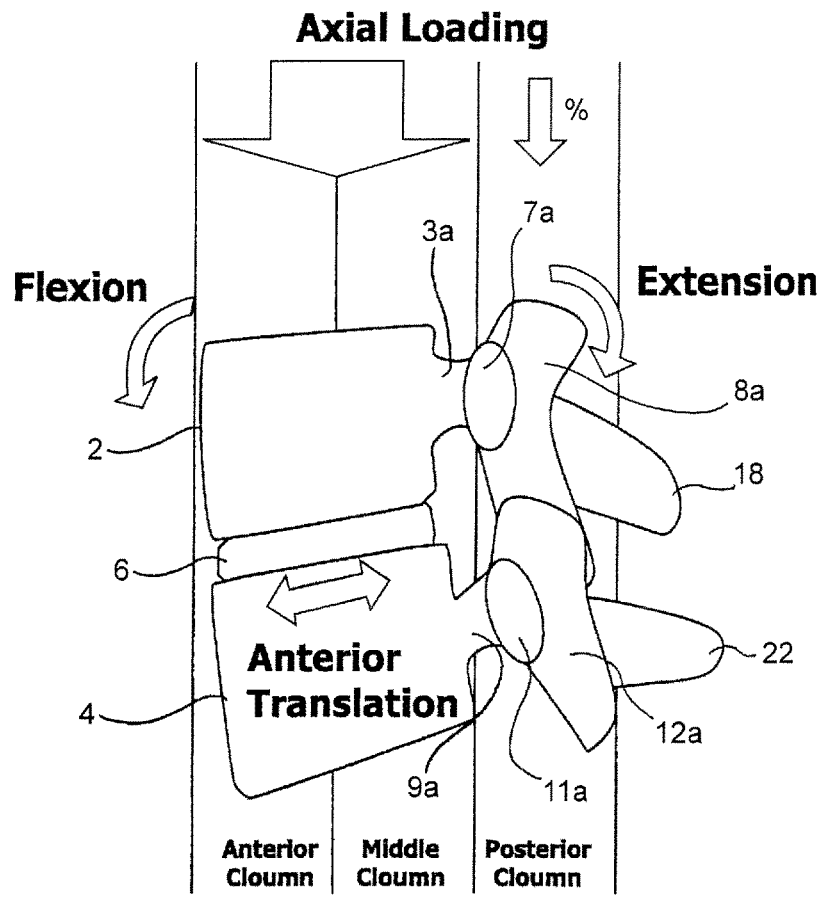
FIGS. 2A, 2B and 2C illustrate left side, dorsal and top views, respectively, of the spinal segments of FIG. 1A under going various motions.
Figure 2B:
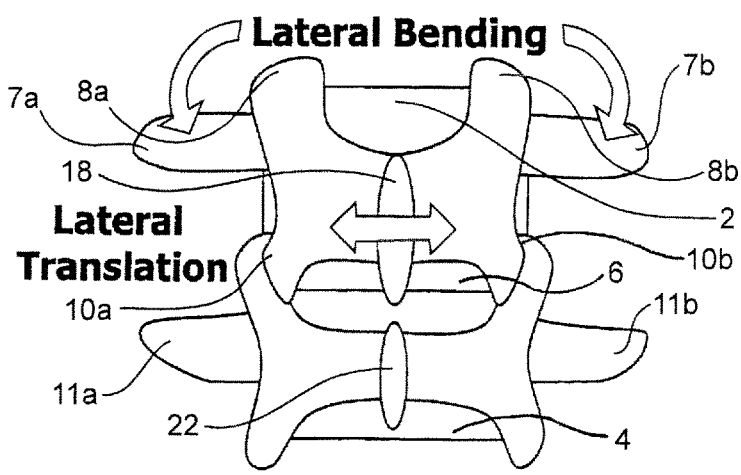
Figure 2C:
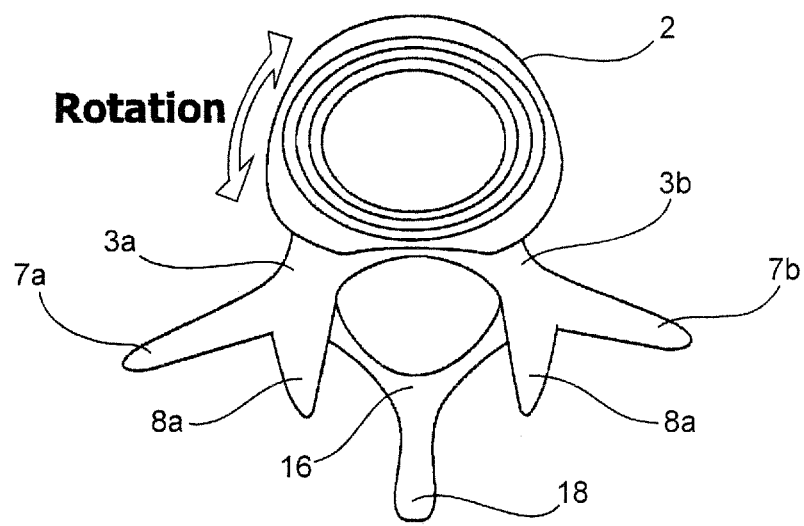

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw" includes reference to one or more screw and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention will now be described in greater detail by way of the following description of exemplary embodiments and variations of the devices and methods of the present invention. The invention generally includes an interspinous spacer device as well as instruments for the percutaneous implantation of the interspinous spacer. A key feature of the interspinous spacer device is that it is expandable from a low profile configuration to a higher profile or operative configuration. This design allows the device, when in the low profile condition, to be delivered by percutaneous means without requiring the removal of any portion of the spinal motion segment into which the device is implanted.

Referring now to the drawings and to FIGS. 3 and 4 in particular, an exemplary interspinous spacer device 24 of the present invention is illustrated in collapsed and expanded configurations, respectively. Interspinous device 24 includes an expandable spacer body 4 that has a size and shape when in the expanded condition for operative positioning between the spinous processes of adjacent superior and inferior vertebrae of the spinal motion segment being treated. Expandable body 34 is made of an expandable or inflatable biocompatible material such as non-porous material, e.g., latex, acrylate or a metal mesh, e.g., a nitinol or titanium cage.

Those spacers made of an inflatable non-porous material, i.e., balloon type spacers (see FIGS. 3-10), are inflated with an inflation or expansion medium, such as air, saline, another biologically compatible fluid, or a flowable solid material, such as polyurethane, or a gel, which thickens or hardens substantially upon injection into balloon 34. In one embodiment, balloon 34 is initially inflated with air to provide some structure or rigidity to it to facilitate its optimum positioning and alignment between the spinous processes. Once positioned as desired, balloon 34 is injected with a flowable solid material (the air therein being displaced possibly via a vent hole within port 32). In certain embodiments, the expandable body is made of a non-compliant or semi-compliant material so as to maintain a substantially fixed shape or configuration and ensure proper, long-term retention within the implant site. In other embodiments, the expandable member may be made of a compliant material. In any embodiment, the compressibility and flexibility of balloon 34 can be selected to address the indications being treated.

Other embodiments of the subject spacers are made of an expandable mesh or cage (see FIGS. 11-12). The mesh or cage maybe made of a super-elastic memory material which is compressible for delivery through a cannula and which is self-expanding upon implantation. Upon expansion, the mesh or cage may be self-retaining whereby its struts, links or wires are sufficiently rigid by themselves to maintain the expanded condition and withstand the natural forces exerted on it by spine. The mesh or cage may have an exterior coating or an interior lining made of materials similar to or the same as that used for the balloon spacers, or may otherwise be embedded in such material. In certain embodiments, an expansion medium may be used to fill the interior of the cage or mesh structure, such as with a biologically compatible fluid or flowable solid material used with the balloon-type embodiments.

In certain embodiments of present invention, either during the implant procedure or in a subsequent procedure, the size or volume of the implanted expandable spacer may be selectively adjusted or varied. For example, after an initial assessment upon implant, it may be necessary to adjust, either reduce or increase, the size or volume of the spacer to optimize the intended treatment. Further, it may be intended to only temporarily implant the spacer for the purpose of treating a temporary condition, e.g., an injured or bulging or herniated disk. Once the repair is achieved or the treatment completed, the spacer may be removed, either with or without substantially reducing the size or volume of the spacer. In other embodiments, the spacer as well as the inflation/expansion material may be made of biodegradable materials wherein the spacer degrades after a time in which the injury is healed or the treatment completed.

Figures 3A, 3B:
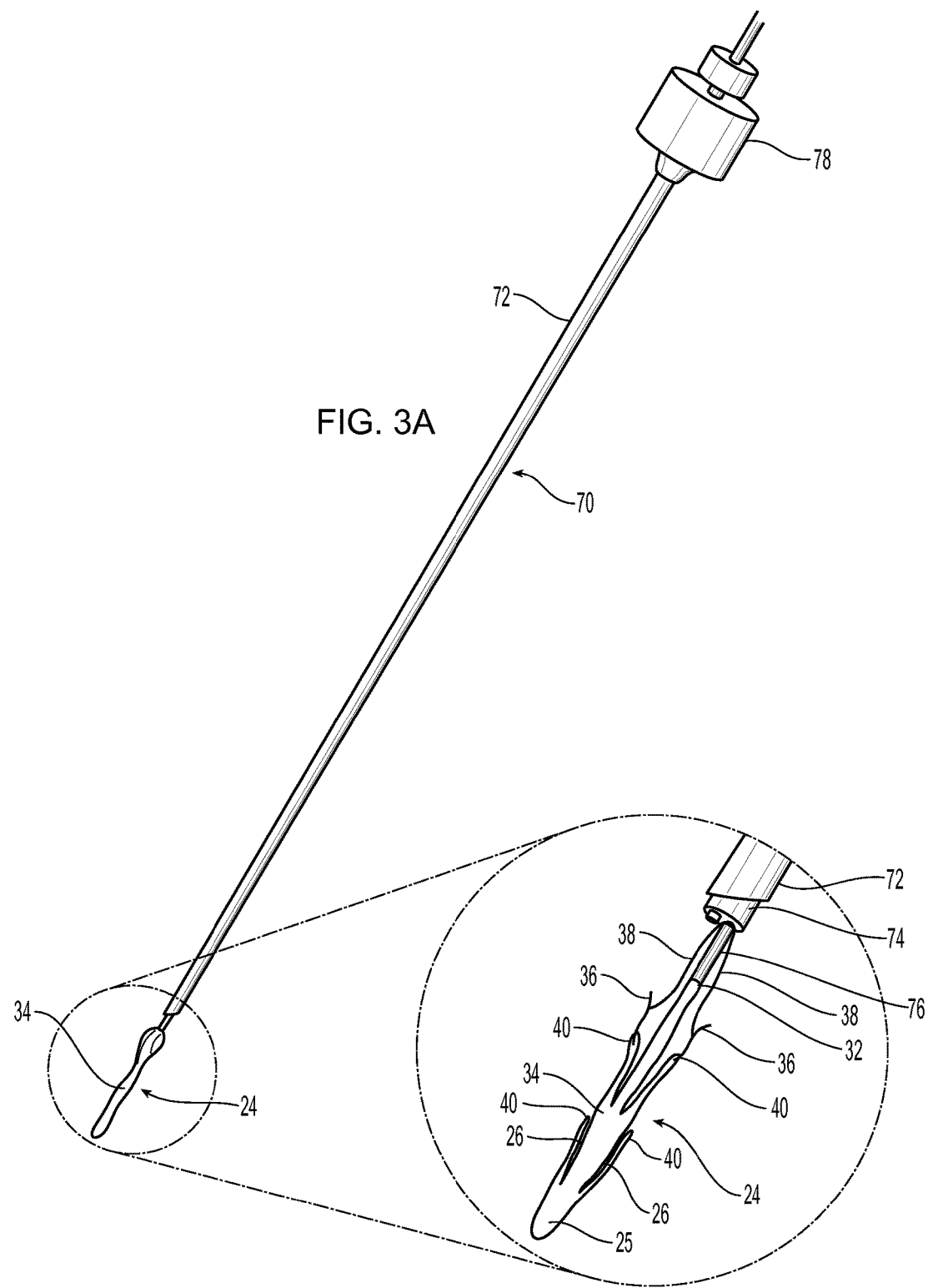
FIG. 3A illustrates an interspinous device of the present invention in an unexpanded or collapsed state coupled to a cannula of the delivery system of the present invention.
FIG. 3B is an enlarged view of the interspinous device of FIG. 3A.

When unexpanded or deflated, as shown in FIGS. 3A and 3B (balloon type) and in FIGS. 11C and 11D (mesh type) expandable body 34 has a low profile, such as a narrow, elongated shape, to be easily translated through a delivery cannula 70. The shape of expandable body 34, when in an expanded or inflated state, has larger profile which is generally H-shaped. Expandable body 34 has lateral or side portions 30, end portions 26 and apexes 28 defined between the side portions 30 and the end portions 26. End portions 26 are preferably recessed or contoured to provide a narrowed central portion along the height dimension or major axis of expandable body 34 to readily fit between and to conform to the spinous processes. Accordingly, expandable body 34 has an apex-to-apex dimension (i.e., height or major axis dimension) from about 3 to about 5 cm and a width dimension (minor axis dimension) from about 2 to about 4 cm For those embodiments of expandable bodies which comprise a balloon configuration, balloon 34 has an inflation or injection port 32 at a sidewall 30 for coupling to a source of inflation or expansion material or medium. Port 32 may consist of a one-way valve which is self-sealing upon release from an inflation mechanism or tube 76. Port 32 is further configured to releasably engage from tube 76, where such engagement may be threaded or involve a releasable locking mechanism. Where the expandable body comprises a mesh or cage, port 32 simply acts as an exit port, however, where an expansion material is used, it also functions as an injection port for the expansion material.

Optionally, device 24 may include a pair of tabs 36 which may be positioned on one side of the device where the tabs 36 are preferably situated at the apexes 28 of expandable body 34. Pins or screws (not yet shown) may be used to secure the tabs against the spinous process to further ensure long-term retention of device 24 within the implant site. Tabs 36 are made of a biocompatible material, such as latex, acrylate, rubber, or a metal, and may be made of the same material used for the expandable member 34. Shown here attached to tabs 36 are tethers 38 which are used in part to manipulate the positioning of expandable body 34 upon implantation into the targeted spinal motion segment. The tethers may be made of any suitable material including but not limited to materials used to make conventional sutures. They may also be made of a biodegradable material. While two tabs and associated tethers are provided in the illustrated embodiment, one, three or more may be employed, where the respective tabs are located on the expandable body so as to be adjacent a bony structure of the vertebra suitable for anchoring thereto. In embodiments which do not employ securing tabs 36, tethers 38 may be attached directly to the expandable body itself.

Optionally still, device 24 may further include radiopaque markers 40 on the surface of expandable body 34 visible under fluoroscopic imaging to facilitate positioning of the expandable body. Any number of markers 40 may be employed anywhere on expandable body 34, however, as few as four markers, one at each apex, may be sufficient. With embodiments employing cage or mesh expandable bodies, the cage or mesh material itself may be radiopaque.

A system of the present invention includes a cannula device 70 having an outer sheath 72, a proximal hub 78 and preferably at least two interior lumens 74, 76 for the percutaneous delivery the device and other tools for implanting the device, which tools may include a cutting instrument 62 (see FIG. 6C), a device delivery instrument 76, an endoscope, etc., which tools will be further discussed in the context of the description of the subject methods with reference to FIGS. 5-10.

In FIGS. 5A-5C, the spinal motion segment of FIG. 1 is illustrated having spinal ligament 54 extending between the superior spinous process 18 and the inferior spinous process 22. A percutaenous puncture is made into the skin 30 adjacent the target spinal motion segment of a patient undergoing the implantation of the interspinous device of the present invention, and a cannula 70 is penetrated to the spinous ligament 54. The puncture and subsequent penetration may be made by way of a sharp distal tip of cannula 70 or by a trocar (not shown) delivered through a lumen of cannula 70.

As illustrated in FIGS. 6A-6C, the spinous ligament 54 is then dissected and an opening 58 created therein by way of a cutting instrument 60, such as a simple scalpel, an electrosurgical device or the like, delivered through a lumen of cannula 70. Cutting instrument 60 may then be removed from cannula 70 and, as illustrated in FIGS. 7A-7D (balloon type) and in FIGS. 11A-11D (cage type), a delivery instrument 16 having interspinous device 24 operatively preloaded is delivered through cannula 70.

The preloading of device 24 to delivery instrument 76 involves providing expandable body 34 in an unexpanded or deflated state and releasably coupled, as described above, by way of inflation or injection port 32 of expandable body 34 to the distal end of delivery instrument 76. In addition to functioning as a pusher, instrument 76 may act as an inflation lumen for balloon type embodiments through which an inflation medium is transported to within expandable body 34.

Depending upon the material used to fabricate expandable body 34, the expandable body may have a degree of stiffness in an unexpanded or deflated state such that it may maintain an elongated configuration so as to be directly insertable and pushable through cannula 70. This may the case where the expandable member 34 is made of a cage or mesh material. Alternatively, a pusher or small diameter rod (not shown) may be inserted through inflation port 32 to within expandable body 34 to keep it in an elongated state so as to prevent expandable body 4 from bunching within cannula 70 and to provide some rigidity to more effectively position the expandable body in the target implant site. The rod is then removed from expandable body 34 and from delivery device 76 upon positioning the expandable body at the target implant site. In either case, expandable body 34 is folded or compressed about its minor axis with the side wall opposite the inflation port 32 defining a distal end 25 (see FIG. 3B) and the apexes 28 of the expandable body folded proximally of distal end 25 to provide a streamline, low profile configuration for delivery through cannula 70.

Once interspinous device 24 is preloaded to delivery device 76 as just described, device 24 is then inserted into a lumen of cannula 70 with tethers 38 pulled back and trail proximally so that the tether ends 38*a* extend from hub 78 of cannula 70. Expandable body member 34 is translated through cannula 70 to within opening 58 within spinous ligament 54 as best illustrated in FIGS. 7C and 11C. For best results, expandable body 34 is centrally positioned within opening 58 so that the countered ends 26 of expandable body 34 readily engage with the opposed spinous processes 18, 22. Fluoroscopy may be employed to visualize markers 40 so as to ensure that expandable body 34 centrally straddles the spinous ligament opening 58, i.e., the markers on the distal side 25 of the expandable body are positioned on one side of the spine and the markers on the proximal side of the expandable body (the side on which port 32 is located) are positioned on the other side of the spine.

Once centrally positioned, expandable body 34 is inflated or expanded, as illustrated in FIGS. 8A-8D and 12A-12D. For balloon spacers, inflation occurs by allowing an inflation or expansion medium, as discussed above, to enter into the interior of the expandable body via port 32. For expandable mesh spacers, the expandable body may be configured to expand automatically upon exiting cannula 70. The inflation or expansion of expandable body 34 may also be visualized under fluoroscopy whereby markers 40, as best shown in FIG. 8C, are observed and the position of expandable body 34 may be adjusted to ensure optimum positioning upon complete inflation. Adjustments of the expandable body's position may be accomplished by manually pulling on one or both tether ends 38*a* which in turn pulls on tabs 26 to which the tethers 38 are attached at their proximal ends. The tethers 38 are selectively pulled as necessary to center or optimally position interspinous expandable body 34 to achieve the desired treatment of the targeted spinal motion segment.

With embodiments in which the expandable body is initially inflated with air and then filled with a solid or fluid medium, the latter is preferably not delivered or injected into the interior of the expandable body until the position of the expandable body within the interspinous space has been verified and optimized. This is beneficial in situations where, upon inflation, it is found that the expandable body is misaligned within the interspinous space and requires repositioning. The expandable body may simply be deflated of air to the extent necessary and repositioned in a less inflated or deflated state. If necessary, for example where it is found that the maximum spacer or expandable body size is insufficient for the particular application at hand, expandable body 34 may be completely deflated and removed and replaced with a more suitably sized unit.

Figure 9A:
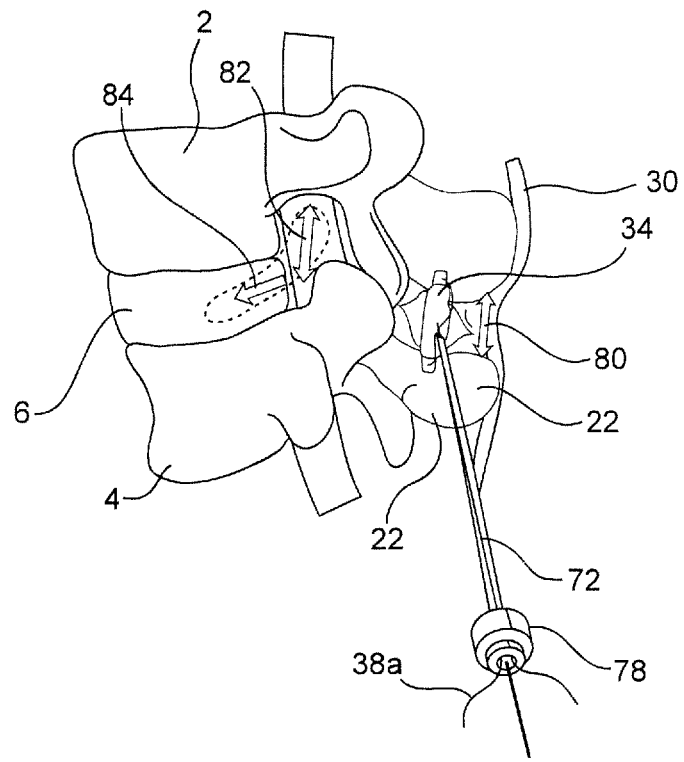
FIG. 9A illustrates a side view of the step of filling the interspinous device of FIG. 4A with an expansion medium.
Figure 9B:
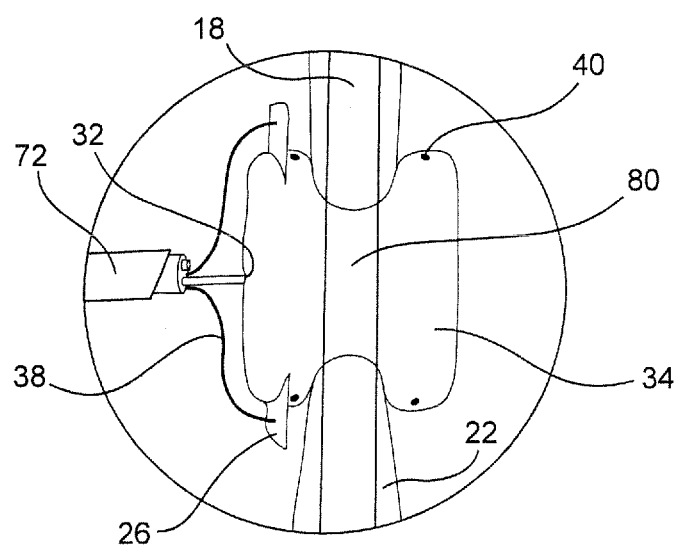
FIG. 9B is an enlarged view of the target area in FIG. 9A.

For balloon spacers and those mesh spacers which are not by themselves sufficiently self-retaining, once the position and extent of inflation or expansion of expandable body 34 are optimized, the expansion medium, e.g., polyurethane, is allowed to flow or injected into the interior of the expandable body via port 32. As illustrated in FIGS. 9A and 9B, expandable body 34 is caused to expand to a selected volume and in so doing forces apart (see arrow 80) the spinous processes 18, 22 in between which it is situated. This selective distraction of the spinous processes also results in distraction of the vertebral bodies 2, 4 (see arrow 82) which in turn allows the disk, if bulging or distended, to retract to a more natural position (see arrow 84). Again, the extent of distraction or lordosis undergone by the subject vertebrae can be monitored by observing expandable body markers 40 under fluoroscopy.

The extent of possible distraction maybe limited by the capacity of expandable body 34 and the type of expandable body material employed. In certain embodiments, such as expandable bodies made of non-compliant or semi-compliant balloons, the requisite volume of the inflation medium may be substantially fixed whereby the balloon achieves its fully expanded configuration upon filling it with the fixed volume of medium. In other embodiments, such as with balloons made of a compliant material, the extent of expansion may be variable and selectable intraoperatively depending on the extent of lordosis or distraction to be achieved between the spinous processes in which balloon 34 is now interposed.

Figure 13A:
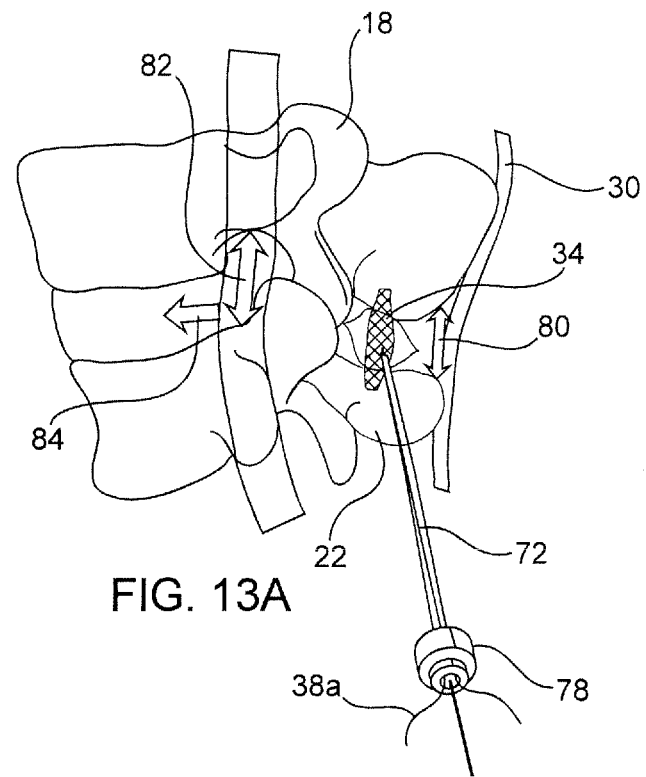
FIG. 13A illustrates a side view of the step of filling the interspinous device of FIGS. 11A-11D with an expansion medium.
Figure 13B:
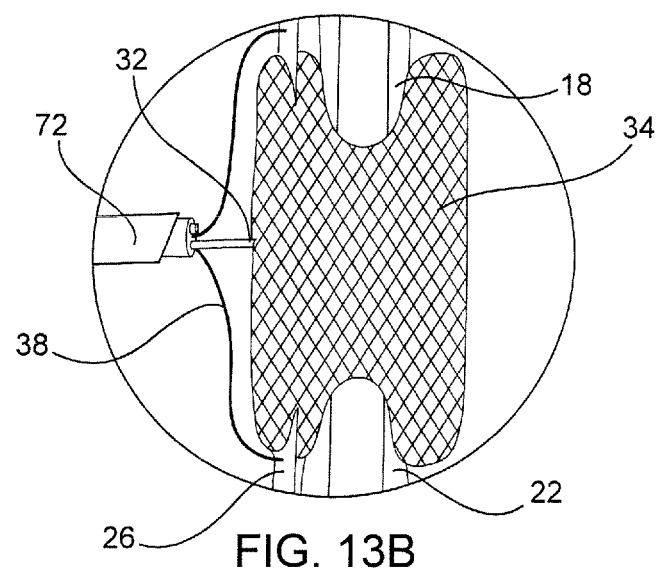
FIG. 13B is an enlarged view of the target area in FIG. 13A.

Upon achieving the desired distraction between the vertebrae, inflation/expansion lumen 76 is disengaged from expandable body port 32 which then becomes sealed by means of a one-way valve that is closed upon disengagement of lumen 76. Inflation/expansion lumen is then removed from cannula 70. While the opposing compressive force exerted on expandable body 34 by the distracted spinous processes 18, 22 may be sufficient to permanently retain expandable body 34 therebetween, the interspinous device may be further secured to the spinous processes 18, 22 to ensure that the expandable body does not slip or migrate from its implanted position. To this end, tabs 36 are anchored to the spinous processes as illustrated in FIGS. 10A and 10B and in FIGS. 13A and 13B. Any type of anchoring means, such as screws, tacks, staples, adhesive, etc. may be employed to anchor tabs 36. Here, cannulated screws 90 are used as anchors and are delivered to the target site releasably coupled to screw driving instrument 88. While various screw attachment and release mechanisms may be employed, a simple configuration involves providing the screws 90 with a threaded inner lumen which is threadably engagable with the threaded distal end of instrument 88.

To ensure accurate placement of screws 90, along with instrument 88, can be tracked and translated over respective tethers 38, which function as guide wires. By manipulating instrument 88, the screws are driven or screwed into the respective spinous process. Screwdriver 88 is then disengaged or unscrewed from screw 90. After both tabs 36 are securely anchored to the spinous processes, the screwdriver and the cannula may be removed from the patient's back.

While certain of the expandable spacers are intended to be permanently implanted within a spine, certain others may be implanted only temporarily to facilitate the healing of an injury or the treatment of a reversible or non-chronic condition, such as a herniated disk. For such temporary treatments, the expansion material most likely is a fluid, such as saline, which may be easily aspirated through port 32 or may be allowed to drain out via a penetration or cut made in the expandable member. In those embodiments in which the expansion material is a flowable solid, which may or may not subsequently harden within the expandable member, the material may be one that is reconstitutable into a liquid form which may then be subsequently aspirated or evacuated from the expandable member. For percutaneous removal of the expandable member, a cannula such as cannula 70 may be used and an aspiration instrument delivered therethrough and coupled to port 32. After deflation and/or evacuation of the expandable member, and removal of the tacks, sutures, staples, etc. if such are used to secure tabs 36, the expandable member may be easily removed through cannula 70. With biodegradable spacers, removal of the spacer is obviated.

It should be noted that any of the above-described steps or procedures, including but not limited to cannulation of the target area, dissection of the spinous ligament, insertion of the expandable body within the dissected opening of the spinous ligament, inflation and/or expansion of the expandable body, adjustment or readjustment of the expandable body, and anchoring of the tabs, etc., may be facilitated by way of a scope 62 delivered through a lumen of cannula 70 to the open distal tip of cannula 70. Alternatively, a second cannula delivered through another percutaneous penetration may be employed for use of an endoscope and any other instruments needed to facilitate the procedure.

The subject devices and systems may be provided in the form of a kit which includes at least one interspinous device of the present invention. A plurality of such devices may be provided where the devices have the same or varying sizes and shapes and are made of the same or varying materials. The kits may further include instruments and tools for implanting the subject devices, including but not limited to, a cannula, a trocar, a scope, a device delivery/inflation/expansion lumen, a cutting instrument, a screw driver, etc., as well as a selection of screws or other devices for anchoring the spacer tabs to the spinous processes. The kits may also include a supply of the expandable body inflation and/or expansion medium. Instructions for implanting the interspinous spacers and using the above-described instrumentation may also be provided with the kits.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for spacing apart a superior spinous process and an inferior spinous process of a subject, the method comprising:
   positioning an interspinous spacer device between the superior and inferior spinous processes, the interspinous spacer device including a main body, a pair of superior elongate members, a pair of inferior elongate members, a movable superior central section extending between the superior elongate members, and a movable inferior central section extending between the inferior elongate members, wherein the movable superior central section extends across most of a first distance between the superior elongate members and/or the movable inferior central section extends across most of a second distance between the inferior elongate members;
   moving the interspinous spacer device from a delivery configuration toward a deployed H-shaped configuration using an instrument coupled to the interspinous spacer device such that the superior elongate members rotate relative to the main body and move along opposite sides of the superior spinous process, the inferior elongate members rotate relative to the main body and move along opposite sides of the inferior spinous process, and regions of the superior and inferior central sections are positioned along a sagittal plane of the subject and translate away from one another and toward the superior and inferior spinous processes, wherein the superior and inferior elongate members are substantially parallel to a longitudinal axis of the interspinous spacer device when the interspinous spacer device is in the delivery configuration, wherein the sagittal plane passes through the superior and inferior spinous processes; and
   separating the instrument from the interspinous spacer device after the superior and inferior central sections extend laterally across the sagittal plane and across the superior and inferior spinous processes, respectively, and the interspinous spacer device is in the deployed H-shaped configuration.

2. The method of claim 1, wherein the superior spinous process is held between the superior elongate members and the inferior spinous process is held between the inferior elongate members when the instrument is separated from the interspinous spacer device.

3. The method of claim 1, wherein positioning the interspinous spacer device between the superior and inferior spinous processes comprises:
   moving at least a portion of a delivery cannula into the subject; and
   translating the interspinous spacer device through and out of the delivery cannula.

4. The method of claim 1, wherein positioning the interspinous spacer device between the superior and inferior spinous processes comprises:
   moving an end of a cannula into the subject; and
   moving the interspinous spacer device along a lumen of the cannula while the cannula is positioned in the subject.

5. The method of claim 4, wherein the interspinous spacer device is moved from the delivery configuration toward the deployed H-shaped configuration while the instrument extends through the cannula.

6. The method of claim 5, wherein the instrument is configured to controllably move the interspinous spacer device from the delivery configuration toward the deployed H-shaped configuration and to controllably move the interspinous spacer device from the deployed H-shaped configuration toward the delivery configuration.

7. The method of claim 1, wherein moving the interspinous spacer device from the delivery configuration toward the deployed H-shaped configuration includes rotating the superior and inferior elongate members from a collapsed axial configuration to a deployed orthogonal configuration.

8. The method of claim 1, wherein the interspinous spacer device comprises a metal H-shaped structure.

9. The method of claim 1, wherein the superior elongate members and the superior central section define a U-shape, and wherein the inferior elongate members and the inferior central section define a U-shape.

10. The method of claim 1, further comprising:
positioning a cannula in the subject;
moving a cutting instrument through the cannula and into the subject; and
cutting tissue of the subject using the cutting instrument to provide access to an interspinous space between the superior and inferior spinous processes.

11. The method of claim 1, wherein the main body is positioned directly between the superior spinous process and the inferior spinous process while the superior and inferior central sections, which are part of the main body, move away from one another.

12. The method of claim 1, further comprising:
anchoring one of the superior elongate members to the superior spinous process; and
anchoring one of the inferior elongate members to the inferior spinous process.

13. The method of claim 1, wherein the instrument is configured to move the interspinous spacer device from the deployed H-shaped configuration to a collapsed configuration while the instrument is coupled to the interspinous spacer device.

14. The method of claim 1, wherein the regions of the superior and the inferior central sections are positioned across the sagittal plane while the inferior spinous process is positioned between the inferior elongate members and while the superior spinous process is positioned between the superior elongate members.

15. The method of claim 1, wherein a superior surface extends continuously along the superior central section and the superior elongate members, wherein an inferior surface extends continuously along the inferior central section and the inferior elongate members, wherein the entire lengths of the superior and inferior surfaces along the superior and inferior central sections move away from one another when the interspinous spacer device moves toward the deployed H-shaped configuration.

16. The method of claim 1, wherein the region of the superior central sections is generally midway between the superior elongate members, and wherein the region of the inferior central section is generally midway between the inferior elongate members.

17. A method for spacing apart a superior spinous process and an inferior spinous process of a subject, the method comprising:
positioning an interspinous spacer device between the superior and inferior spinous processes, the interspinous spacer device including a main body, a pair of superior elongate members, a pair of inferior elongate members, a movable superior central section extending between the superior elongate members, and a movable inferior central section extending between the inferior elongate members, wherein the superior elongate members are foldable against the main body, wherein the movable superior central section extends across most of a first distance between the superior elongate members and/or the movable inferior central section extends across most of a second distance between the inferior elongate members;
moving the interspinous spacer device from a delivery configuration toward a deployed H-shaped configuration using an instrument coupled to the interspinous spacer device such that the superior elongate members rotate relative to the main body and move along opposite sides of the superior spinous process, the inferior elongate members rotate relative to the main body and move along opposite sides of the inferior spinous process, and regions of the superior and inferior central sections are positioned along a sagittal plane of the subject and translate away from one another and toward the superior and inferior spinous processes, wherein the sagittal plane passes through the superior and inferior spinous processes; and
separating the instrument from the interspinous spacer device after the superior and inferior central sections extend laterally across the sagittal plane and across the superior and inferior spinous processes, respectively, and the interspinous spacer device is in the deployed H-shaped configuration.

18. A method for spacing apart a first spinous process and a second spinous process, the method comprising:
positioning an interspinous spacer device at an interspinous space between the first and second spinous processes;
rotating a pair of first elongate members of the interspinous spacer device from a first delivery configuration toward a first deployed configuration, wherein the first elongate members in the first delivery configuration are substantially parallel to a longitudinal axis of the interspinous spacer device;
rotating a pair of second elongate members of the interspinous spacer device from a second delivery configuration toward a second deployed configuration, wherein the second elongate members in the second delivery configuration are substantially parallel to the longitudinal axis of the interspinous spacer device;
moving first and second central sections toward the first and second spinous processes, respectively, while both the first and second central sections are positioned across a subject's sagittal plane passing through the first and second spinous processes, respectively, and wherein the first central section extends across most of a distance between the first elongate members; and
separating a delivery instrument from the interspinous spacer device when the interspinous spacer device is in a deployed H-shaped configuration and when the first and second elongate members are in the first and second deployed configurations, respectively.

19. The method of claim 18, wherein positioning the interspinous spacer device at the interspinous space comprises:
moving at least a portion of a delivery cannula into the subject;
translating the interspinous spacer device along the delivery cannula which is positioned in the subject; and
moving the interspinous spacer device out an end of the delivery cannula which is positioned in the subject.

20. The method of claim 18, wherein positioning the interspinous spacer device comprises:
moving an end of a cannula into the subject; and
moving the interspinous spacer device along the cannula and out the end of the cannula.

21. The method of claim 20, wherein the interspinous spacer device is moved from the delivery configuration toward the deployed H-shaped configuration while the instrument extends through the cannula.

22. The method of claim 18, wherein the interspinous spacer device comprises a deployable metal H-shaped structure.

23. The method of claim 18, further comprising:
positioning a cannula in the subject;
delivering a cutting instrument through the cannula and into the subject; and
cutting tissue of the subject to provide access to the interspinous space for positioning the interspinous spacer device at the interspinous space.

24. The method of claim 18, further comprising:
moving a first anchor into the first spinous process to couple one of the first elongate members to the first spinous process; and
moving a second anchor into the second spinous process to couple one of the second elongate members to the second spinous process.

25. The method of claim 24, wherein at least one of the first and second anchors includes a screw, a tack, or a staple.

26. The method of claim 18, further comprising rotating the first elongate members toward the first deployed configuration using the delivery instrument after the entire interspinous spacer device has been delivered out of a delivery cannula.

27. The method of claim 18, wherein a region of the first central section that moves toward the first spinous process is positioned generally midway between the first elongate members.

28. The method of claim 18, wherein the first and second central sections are contoured to seat against the first and second spinous processes, respectively.

29. The method of claim 18, wherein the first elongate members and/or second elongate members are foldable against a main body of the interspinous spacer device.

30. A method comprising:
positioning an interspinous spacer device at an interspinous space between first and second spinous processes of a subject;
moving a pair of first elongate members of the interspinous spacer device from a first delivery configuration toward a first deployed configuration, wherein the first elongate members in the first delivery configuration are substantially parallel to a longitudinal axis of the interspinous spacer device;
moving a pair of second elongate members of the interspinous spacer device from a second delivery configuration toward a second deployed configuration;
moving first and second central sections of the interspinous spacer device toward the first and second spinous processes, respectively, wherein a portion of the first central section that moves toward the first spinous process extends across most of a distance between the first elongate members; and
expanding a narrowed section of the interspinous spacer device to translate the first and second central sections in the opposite directions, wherein the first and second central sections are part of the narrowed section, and wherein the narrowed section is positioned between the first elongate members and is positioned between the second elongate members.

31. The method of claim 30, wherein the first and second central sections both extend across a sagittal plane passing through the first and second spinous processes while the first and second central sections move toward the respective first and second spinous processes.

32. The method of claim 30, wherein when the first and second central sections move toward the respective first and second spinous processes, the first elongate members are on opposite sides of the sagittal plane and the second elongate members are on opposite sides of the sagittal plane.

33. The method of 30, wherein the first elongate members and/or second elongate members are foldable against a main body of the interspinous spacer device.

* * * * *